US008367098B2

(12) United States Patent
Maguire et al.

(10) Patent No.: US 8,367,098 B2
(45) Date of Patent: Feb. 5, 2013

(54) UNIQUE COMBINATIONS OF ANTIMICROBIAL COMPOSITIONS

(75) Inventors: Robin A. Maguire, Ossining, NY (US); Mitchell Thorn, Astoria, NY (US); David M. Phillips, Piermont, NY (US); Naomi Rutenberg, Washington, DC (US)

(73) Assignee: The Population Council, Inc., New York, NY (US)

( * ) Notice: Subject to any disclaimer, the term of this patent is extended or adjusted under 35 U.S.C. 154(b) by 202 days.

(21) Appl. No.: 12/587,405

(22) Filed: Oct. 6, 2009
(Under 37 CFR 1.47)

(65) Prior Publication Data
US 2010/0256089 A1  Oct. 7, 2010

Related U.S. Application Data

(63) Continuation-in-part of application No. 10/977,001, filed on Oct. 29, 2004, now abandoned, which is a continuation of application No. PCT/US03/13456, filed on Apr. 30, 2003.

(60) Provisional application No. 60/377,050, filed on May 1, 2002, provisional application No. 60/376,400, filed on Apr. 30, 2002.

(51) Int. Cl.
*A61F 6/06* (2006.01)
*A61F 13/00* (2006.01)
(52) U.S. Cl. .................. 424/430; 424/433; 424/434
(58) Field of Classification Search .................. None
See application file for complete search history.

(56) References Cited

U.S. PATENT DOCUMENTS

| 3,626,054 | A | 12/1971 | Ores |
|---|---|---|---|
| 3,935,307 | A | 1/1976 | Aimoto et al. |
| 4,356,264 | A | 10/1982 | Martin |
| 4,532,128 | A | 7/1985 | Sheldon et al. |
| 4,783,446 | A | 11/1988 | Neushul |
| 4,840,941 | A | 6/1989 | Ueno |
| 5,009,867 | A | 4/1991 | Kratochvil |
| 5,066,413 | A | 11/1991 | Kellett |
| 5,069,906 | A | 12/1991 | Cohen et al. |
| 5,124,078 | A | 6/1992 | Baust |
| 5,208,031 | A | 5/1993 | Kelly |
| 5,482,053 | A | 1/1996 | Kelly |
| 5,599,551 | A | 2/1997 | Kelly |
| 5,624,675 | A | 4/1997 | Kelly |
| 5,658,893 | A | 8/1997 | Anderson et al. |
| 5,667,773 | A | 9/1997 | Farrar et al. |
| 5,785,054 | A | 7/1998 | Kelly |
| 5,861,383 | A | 1/1999 | Cardin |
| 5,972,372 | A | 10/1999 | Saleh et al. |
| 5,980,477 | A | 11/1999 | Kelly |
| 6,214,802 | B1 | 4/2001 | Nakamura et al. |
| 6,239,141 | B1 | 5/2001 | Allen et al. |
| 6,248,339 | B1 | 6/2001 | Knitowski et al. |
| 6,248,360 | B1 | 6/2001 | Choi et al. |
| 6,265,368 | B1 | 7/2001 | Aronson et al. |
| 6,321,750 | B1 | 11/2001 | Kelly |
| 6,355,272 | B1 | 3/2002 | Caramella et al. |
| 6,696,071 | B2 | 2/2004 | Kelly |
| 2003/0185876 | A1 | 10/2003 | Calton et al. |
| 2005/0171053 | A1 | 8/2005 | Blakemore et al. |
| 2005/0261240 | A1 | 11/2005 | Maguire et al. |
| 2006/0057132 | A1* | 3/2006 | De Simone ................ 424/93.45 |
| 2006/0147504 | A1* | 7/2006 | Corry et al. .................. 424/443 |

FOREIGN PATENT DOCUMENTS

| CA | 2384474 A1 | 10/2003 |
|---|---|---|
| EA | 0240098 A2 | 10/1987 |
| EP | 0091409 B1 | 2/1986 |
| EP | 0 293 826 A2 | 12/1988 |
| EP | 0661028 A1 | 7/1995 |
| JP | 2001-114696 A | 4/2001 |
| WO | 88/06396 A2 | 9/1988 |
| WO | 94/15624 A1 | 7/1994 |
| WO | 98/37862 A1 | 9/1998 |
| WO | 99/21586 A2 | 5/1999 |
| WO | 99/60042 A1 | 11/1999 |
| WO | 00/38653 A1 | 7/2000 |
| WO | 01/56406 A1 | 8/2001 |
| WO | 01/73265 A1 | 10/2001 |

OTHER PUBLICATIONS

Fernandez-Romero et al. Sexually Transmitted Diseases 2007 34:9-14.*
Malawista et al. Inflammation 2007 30:131-135.*
Zabik et al. Journal of Food Science 1965 30:111-117.
Mainly. (2000). In Collins English Dictionary. Retrieved from http://www.credoreference.com/entry/hcengdict/mainly.
Aqueous. (2000) In Collins English Dictionary. Retrieved from http://www.credoreference.com/entry/hcengdict/aqueous.
Engster et al. Toxicology and Applied Pharmacology 1976 38:265-282.
Carlucci M J et al: "Protective effect of a natural carrageenan on genital herpes simplex virus infection in mice" Antiviral Research, Elsevier Science BV., Amsterdam, NL, vol. 64, No. 2, Nov. 2004, pp. 137-141, XP004605751 ISSN: 0166-3542.
International Search Report and Written Opinion, PCT/US2010/051303, dated Nov. 19, 2010.
Maguire, et al., "Comparison of Microbicides for Efficacy in Protecting Mice against Vaginal Challenge with Herpes Simplex Virus Type 2, Cytotoxicity, Antibacterial Properties, and Sperm Immobilization," Sex. Trans. Dis. 28:259-265 (2001).
Elias et al., Colposcopic Evaluation of a Vaginal Gel Formulation of iota—Carrageenan, Contraception 56:387-89 (1997).
Perotti, et al., "Carrageenan Formulation Prevents Macrophage Trafficking from Vagina: Implications for Microbicide Development," Biol. Reprod. 69:933-39 (2003).
Debon, et al., "In vitro binding of calcium, iron and zinc by non-starch polysaccharides," Food Chemistry 73:701-10 (2001).

(Continued)

*Primary Examiner* — Juliet C Switzer
*Assistant Examiner* — Caralynne Helm
(74) *Attorney, Agent, or Firm* — Lerner, David, Littenberg, Krumholz & Mentlik, LLP

(57) ABSTRACT

Disclosed are compositions for inhibiting transmission of a sexually transmitted infection that contain one or more polyanionic microbicides, such as carrageenans, including lambda carrageenan, as well as water-soluble metal salts and specified antiretroviral agents comprising NNRTIs and NRTIs. Also disclosed are methods for making and using the compositions.

18 Claims, 6 Drawing Sheets

OTHER PUBLICATIONS

Berbel, et al., "Voltammetry of metal ions in mixtures of ligands Part III: Application to systems including inert complexes," Electroanalytical Chem. 453:151-9 (1998).

Zacharopoulos, et al., "Vaginal Formulations of Carrageenan Protect Mice from Herpes Simplex Virus Infection," Clin. Diagn. Lab. Immunol. 494:465-68 (1997).

Zaretsky, et al., "Sulfated Polyanions Block Chlamydia Trachomatis Infection of Cervix-Derived Human Epithelia," Infection and Immunity, American Society for Microbiology, vol. 63 (No. 9) pp. 3520-3526 (Sep. 1995).

Maguire et al., "Carrageenan-Based Nonoxynol-9 Spermicides for Prevention of Sexually Transmitted Infections," Sexually Transmitted Diseases, Lippincott Williams & Wilkins, vol. 25 (No. 9), pp. 494-500 (Oct. 1998).

Nakashima et al., Purification and Characterization of an Avian Myeloblastosis and Human Immunodeficiency Virus Reverse Transcriptase Inhibitor, Sulfated Polysaccharides Extracted from Sea Algae, Antimicrobial Agents and Chemotherapy, American Society for Microbiology, vol. 31 (No. 10), pp. 1524-1528 (Oct. 1987).

Nakashima et al., "Sulfation of Polysaccharides Generates Potent and Selective Inhibitors of Human Immuno-Deficiency Virus Infection and Replication, in vitro," Jpn. J. Cancer Res., Gann, vol. 78, pp. 1164-1168 (Nov. 1987).

Pearce-Pratt, et al., "Sulfated Polysaccharides Inhibit Lymphocyte-to-Epithelial Transmission of Human Immunodeficiency Virus1," Biology of Reproduction, vol. 54, The Population Council (New York, NY), pp. 173-182 (1996).

Abstract, Hoffman et al., "Selective Inhibition of Cell Proliferation and DNA Synthesis by the Polysulfated Carbohydrate Iota-Carrageenan," Cancer Chemother. Pharmacol., vol. 36 (No. 4), pp. 325-334 (1995).

Abstract—Carlucci et al., "Antiherpetic and Anticoagulant Properties of Carrageenans from the Red Seaweed Gigartina Skottsbergii and Their Cyclized Derivatives: Coorelation Between Structure and Bilogical Activity," Int. J. Biol. Macromol., vol. 20 (No. 2), pp. 97-105 (1997).

Abstract—Marchetti et al., "Inhibition of Herpes Simplex Virus Infection by Negatively Charged and Neutral Carbohydrate Polymers," J. Chemother., Florence, vol. 7 (No. 2), pp. 90-96 (1995).

Abstract—Matusmoto et al., "Potential Activity of Carrageenan to Enhance Antibacterial Host-Defense Systems in Mice," J. Infect. Chemother., vol. 1 (No. 1) pp. 59-63 (1995).

Abstract—Yamada et al., "Skeletal Muscle Growth Stimulants Containing Carrageenan," Jpn. Kokai Tokkyo Koho Patent No. 95179350 (Jul. 18, 1995), one page.

Abstract—Yamada et al., "Preparation and Anti-HIV Activity of Low-Molecular-Weight Carrageenans and Their Sulfated Derivatives," Carbohydr. Polym., vol. 32 (No. 1) pp. 51-55 (1997).

Article—Stein et al., "Causative and Beneficial Algae in Human Disease Condtiions: A Review," Phycologia, vol. 23, pp. 485-501 (1984).

Pamphlet—"Carraguard—A microbicide in Development," The Population Cojncil, 2 pages (2002).

Article—"New Microbicide Entering Phase Three Trials," Sexuality Information and Education Council of the United States, 3 pages (Jan. 31, 2002).

Zacharopoulus et al. Clinical and Diagnostic Laboratory immunology 1997 4(4):465-468.

Bonferoni et al. AAPS PharmSci Tec 2000 1 (article 15):1-8.

* cited by examiner

| TREATMENT | RT-PCR +/TOTAL | PERCENTAGE POSITIVE |
|---|---|---|
| PBS | 16/22 | 72% |
| METHYL CELLULOSE | 7/10 | 70% |
| CARRAGEENAN MIXTURE | 2/22 | 9% |

UNIQUE COMBINATIONS OF ANTIMICROBIAL COMPOSITIONS

CROSS-REFERENCE TO RELATED APPLICATIONS

This application is a continuation-in-part of U.S. patent application Ser. No. 10/977,001, filed on Oct. 29, 2004, now abandoned which is a continuation of International Application No. PCT/US03/13456, filed on Apr. 30, 2003, which claims the benefit of the filing date of U.S. Provisional Patent Application No. 60/376,400, filed on Apr. 30, 2002, and U.S. Provisional Patent Application No. 60/377,050, filed on May 1, 2002, the disclosures of which are incorporated herein by reference.

Financial support for the invention described herein was received from the United States Agency for International Development under Cooperative Agreement No. GPO-A-00-04-00019 and NIH Grant No. NIH U19 A1065412. Therefore, the United States Government may have certain rights to the invention.

BACKGROUND OF THE INVENTION

Carrageenans are polysaccharides obtained from the red algae commonly known as seaweed. They are a structural component of seaweed and are extracted as three main types, namely iota, kappa and lambda, although there are other types as well, including kappa-II, mu and nu carrageenans. Carrageenans have been used extensively in the food, pharmaceutical and cosmetics industries as thickeners, gelling agent, and stabilizing and dispersing agents. Extensive pharmacological and toxicological studies have been conducted. Carrageenan has been found to be non-toxic by oral, dermal, and inhalation routes of administrations even at extremely high doses. The carrageenans were therefore classified as "generally recognized as safe" (GRAS) by the FDA in 1972[2]. Further extensive oral pharmacokinetic studies conducted in pigs, rats, mice, gerbils, guinea pigs, ferrets, hamsters, dogs, and monkeys[3-11] showed that the breakdown of the carrageenans in the gastrointestinal tract were minimal at best and that absorption was virtually non-existent International Patent Publication WO 94/15624 teaches use of sulfated polysaccharides such as iota carrageenan, dextran sulfate, kappa carrageenan, lambda carrageenan, heparin mimetics, heparin sulfate, pentosan polysulfate, chondrotin sulfate, lentinan sulfate, curdlan sulfate, de-N-sulfated heparin and fucoidan, to inhibit cell-to-cell transmission of HIV and thus the sexual transmission of Acquired Immune Deficiency Syndrome (AIDS), as well as *Chlamydia* organism. This publication teaches that iota carrageenan is the most efficacious of the commercially available sulfated carrageenans in preventing HIV infection and in blocking *Chlamydia* infection in vitro and in vivo.

SUMMARY OF THE INVENTION

Applicants have discovered that a certain carrageenan or mixtures or combinations of various carrageenans possess specific physical and chemical properties and that when they are formulated for vaginal administration, they provide a prolonged antimicrobial effect and inhibit or reduce the possibility of transmission of a sexually transmitted infection (STI).

Accordingly, a first aspect of the present invention is directed to an aqueous antimicrobial composition, comprising an effective amount of an antimicrobial agent comprising carrageenans (referred to herein as "the carrageenans" or a "carrageenan mixture") which are lambda carrageenan in an amount of at least about 50% by dry weight of said carrageenans, remainder of said carrageenans being at least one non-lambda carrageenan, and a physiologically acceptable pH controlling agent. For purposes of the present invention, the term "antimicrobial" is meant to embrace anti-bacterial and/or antiviral activity.

A related aspect of the present invention is directed to a sexually transmitted infection (STI) inhibiting composition, comprising an effective amount of an antimicrobial agent comprising carrageenans which are lambda carrageenan in an amount of at least about 50% by dry weight of said carrageenans, remainder of said carrageenans being at least one non-lambda carrageenan, and a physiologically acceptable pH controlling agent.

The compositions may further include another antimicrobial agent and/or a vaginally administrable drug, in which case the carrageenan component may be a lambda carrageenan, without any non-lambda carrageenan. The additional agent may be in admixture and/or associated with the carrageenans such as in the form of a complex. Accordingly, a further aspect of the present invention is directed to aqueous antimicrobial composition, comprising: (a) a physiologically acceptable pH controlling agent; and (b) an effective amount of an antimicrobial agent comprising a complex of a lambda carrageenan or carrageenans which are lambda carrageenan in an amount of at least about 50% by dry weight of said carrageenans, remainder of said carrageenans being at least one non-lambda carrageenan, and an antimicrobial, physiologically acceptable water-soluble cationic metal salt.

A further aspect of the present invention is directed to an aqueous antimicrobial composition, comprising: (a) a physiologically acceptable pH controlling agent; (b) an effective amount of an antimicrobial agent comprising a complex of a lambda carrageenan or carrageenans which are lambda carrageenan in an amount of at least about 50% by dry weight of said carrageenans, remainder of said carrageenans being at least one non-lambda carrageenan; and (c) a lignosulfonic acid.

A further aspect of the present invention is directed to an aqueous antimicrobial composition, comprising: (a) a physiologically acceptable pH controlling agent; (b) an effective amount of an antimicrobial agent comprising a complex of a lambda carrageenan or carrageenans which are lambda carrageenan in an amount of at least about 50% by dry weight of said carrageenans, remainder of said carrageenans being at least one non-lambda carrageenan; and (c) a vaginally administrable drug such as a contraceptive agent or an agent for hormone replacement therapy.

A further aspect of the present invention is directed to an aqueous antimicrobial composition comprising an effective amount of an antimicrobial agent comprising a polyanionic microbicide, such as carrageenans which are lambda carrageenans in an amount of at least about 50% by dry weight of the carrageenans, the remainder of the carrageenans being at least one non-lambda carrageenan, a physiologically acceptable water soluble cationic metal salt, and a non-nucleoside reverse transcriptase inhibitor or a nucleoside reverse transcriptase inhibitor.

A further aspect of the present invention is directed to a method of processing, refining or stabilizing the carrageenans of the present invention. The method entails mixing a lambda carrageenan or the carrageenans in anhydrous or powdery form with the dry form of the pH controlling agent, followed by hydration of the carrageenans e.g., by the addition of water or another aqueous solution. The method overcomes several disadvantages associated with current techniques for processing high concentrations of carrageenans into homogenous aqueous solutions and facilitates further processing into pharmaceutical formulations such as the aforementioned compositions and complexes.

DETAILED DESCRIPTION OF THE INVENTION

Figure 1:
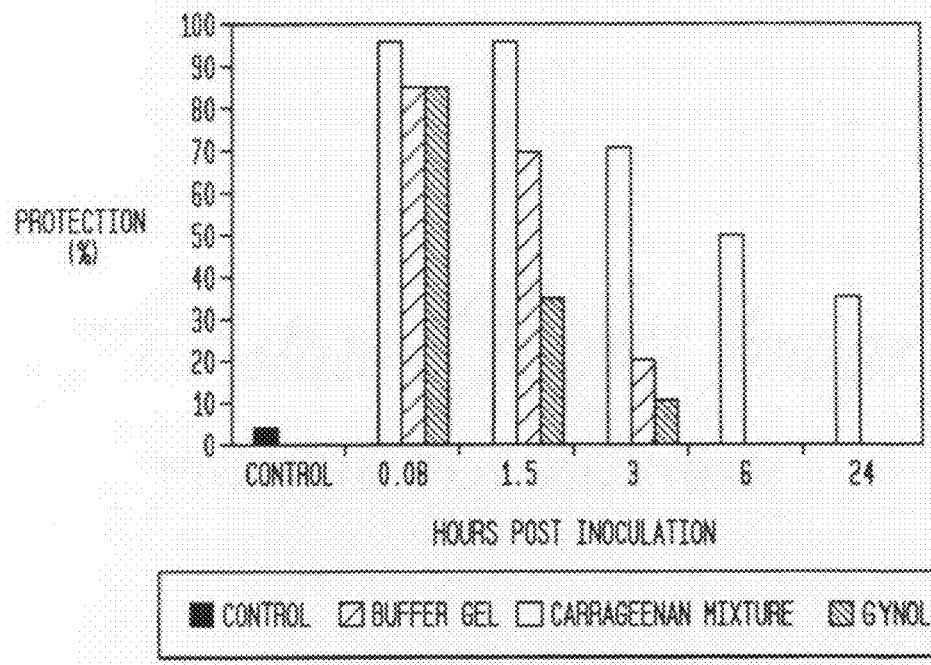
FIG. 1 is a graph showing long-term activity of a composition containing the carrageenans of the present invention. Mice were challenged with a 95-100% infectious dose of HSV-2 at various time intervals after application of the composition. The composition retains some level of activity against HSV-2 even after 24 hours. This suggests that a woman could be protected even if considerable time elapsed between use of the composition and coitus.

The polyanionic microbicides used in the compositions of the present invention are microbicides which interfere with viral attachment so as to reduce HIV transmission across mucosal surfaces. These polyanionic microbicides include compounds such as PRO 2000, Buffergel, dextrin sulfate, cellulose sulfate, and most preferably the carrageenans.

The carrageenans present in compositions of the present invention include a lambda carrageenan. To the extent that non-lambda carrageenans are present (in which the case the carrageenan component of the compositions may be referred to as "the carrageenans" or the "carrageenans mixture"), the carrageenans mixture contains at least about 50% (and preferably at least 50%) of lambda carrageenan, based on total dry weight of the carrageenans in the composition. In more preferred embodiments, the amount of lambda carrageenan is at least about 75, 76, 77, 78, 79, 80, 81, 82, 83, 84, 85, 86, 87, 88, 89, 90, 91, 92, 93, 94, 95, 96, 97, 98, or 99% of the total dry weight of the carrageenans (i.e., lambda and non-lambda carrageenans). Other preferred amounts are at least 75%, at least about 85%, at least about 95%, about 85 to about 99%, and from about 94 to about 97% lambda carrageenan.

Lambda carrageenan is commercially available (FMC Corp., Philadelphia). Alternatively, lambda carrageenan can be produced from diploid (sporophyte) seaweed plants e.g., *Gigartina radula, Gigartina skottsbergii, Gigartina chamissoi, Gigartina stellata, Iridaea cordata, Chondrus chrispus* and *Sarcothalia crispata*. Isolation of the carrageenan from the seaweed is conducted in accordance with standard techniques. For example, the seaweed is separated, cleaned and then dried. Lambda carrageenan is extracted in hot dilute sodium hydroxide, yielding a paste that contains as much as 4% concentration of lambda carrageenan. The resulting paste is clarified by centrifugation and filtration to yield a clear, lambda carrageenan solution. Water is removed by any combination of evaporation, alcohol precipitation or washing, and drying.

The remainder of the carrageenans in compositions of the present invention may include at least one non-lambda carrageenan. By "non-lambda carrageenan", it is meant any carrageenan other than lambda carrageenan, such as kappa-carrageenan, iota carrageenan, kappa-II carrageenan (which contains kappa and iota carrageenans), mu carrageenan, and nu carrageenan. Non-lambda carrageenans are also available commercially (e.g., FMC Corp.) or may be extracted from seaweed in accordance with standard techniques. For example, kappa-II carrageenan is also naturally present in the species of seaweed described above. In preferred embodiments, the non-lambda carrageenans include kappa carrageenan, iota carrageenan, and kappa-II carrageenans, and mixtures of any two or more thereof. In more preferred embodiments, the non-lambda carrageenan includes kappa-II carrageenan. In preferred embodiments, the non-lambda component of the carrageenans constitutes less than about 1, 2, 3, 4, 5, 6, 7, 8, 9, 10, 11, 12, 13, 14, 15, 16, 17, 18, 19, 20, 21, 22, 23, 24 or about 25% of the total dry weight of the carrageenans. In more preferred embodiments, the non-lambda component is about less than about 25%, less than about 15%, less than about 5%, about 1 to about 15%, or about 3 to about 6% of the total dry weight of the carrageenans. In other preferred embodiments, the carrageenan mixture is substantially or entirely free of dextrose, an ingredient commonly found in carrageenans used in the food industry.

In order to provide an antimicrobial effect, the lambda carrageenan or the carrageenans are generally present in amounts of about 1 to about 5%, based on total weight of the composition. In preferred embodiments, the carrageenans are present in amount of about 3% by total weight of the composition. By "antimicrobial" or "antimicrobial effect", it is meant that the composition inhibits or reduces the likelihood of transmission of a sexually transmitted infection caused by a bacterium, another microbe or a virus. The compositions of the present invention useful in protection against sexually transmitted infections e.g., by inhibiting infection by HIV, HPV, HSV-2 and *Neisseria gonorrhoeae*. On the other hand, the terms "antimicrobial" and "antimicrobial effect" are not meant to convey, imply or be limited to any particular means by which the inhibition of transmission of the infection is accomplished. Without intending to be bound by any particular theory of operation, it is believed that the carrageenans non-specifically bind to virus, bacteria and other microbes that are etiological agents of STIs, thereby blocking receptor sites. Compositions containing the lambda carrageenan or the carrageenans in amounts less than 1% or greater than 5% may be used, so long as that they provide an antimicrobial effect and retain vaginal acceptability. By "vaginal acceptability", it is meant that the rheological properties such as viscosity of composition allow it to be used for its intended purpose (e.g., the composition maintains a viscosity so that it can be applied by the user and be retained in the vaginal vault, as well as providing aesthetic properties such as being substantially odorless, smoothness, clarity, colorlessness and tastelessness). The viscosity is selected so as to enable the composition to evenly coat the epithelial lining of the vaginal vault. In general, the viscosity of the compositions is about 10,000 to about 50,000 cP, preferably about 20,000 to about 50,000 cP, and more preferably about 30,000 to about 50,000 cP. Carrageenan has a continuum of molecular weights. In general, the carrageenan mixtures of the present invention may have a molecular weight of up to about $2 \times 10^6$ daltons with less than about 1% of carrageenan molecules having an average molecular weight of $1 \times 10^5$ daltons (as determined by gas permeation chromatography and light scattering). More particularly, a lambda carrageenan in the invention has a weight average molecular weight of about 600,000 to about 1,200,000 daltons. This physical property imparts non-absorbability to the final formulation that in turn provides prolonged anti-microbial activity.

Among the other polyanionic microbicides, other than the carrageenans, which can also be used in the compositions of the present invention, is PRO 2000. This microbicide is a vaginal microbicide for HIV prevention. In addition, other such polyanionic microbicides include Buffergel, a microbicidal spermicide which provides buffering activity to maintain the mild, protective acidity of the vagina in the presence of semen. In addition, dextrin sulfate, a polyanion which blocks the entry of HIV at the surface of the cell, and cellulose sulfate can also be utilized therefor.

The composition further contains a physiologically acceptable pH controlling agent such as phosphate buffered saline (PBS). In addition to stabilizing the pH of the composition (e.g., at a level of about 3.5 to about 8.5, and preferably about 5.8 to about 7.2, such as from about 6.8 to 7.2), the pH controlling agent prevents or reduces any change of the change in the composition once it is introduced into the body where the pH can vary significantly. Vaginal pH can range between 3.5 to 5.5. Thus, the presence of the pH controlling agent extends the antimicrobial effect of the carrageenans. The compositions include from bout 0.001% to about 1.0% of the pH-controlling agents. The compositions formulation may further contain other active agents and/or inert ingredients, depending upon the intended use (as described below).

The carrageenans of the present invention provide several other benefits. They remain stable if exposed to freezing, ambient, or boiling temperatures. The mixture is compatible with the human vaginal environment. Without intending to be bound by any particular theory of operation, it is believed that the carrageenans are compatible with the human vaginal environment and do not act as a substrate or otherwise cause or stimulate growth of natural vaginal flora, nor are they toxic so as to disrupt the natural floral balance in the vagina. Aside from the properties attributable to the carrageenans of the present invention, their antimicrobial activity extends over a period of time because they are not systemically absorbed or degraded to any absorbable by-products detrimental to humans.

Another aspect of the present invention is directed to a complex between a water-soluble metal salt and the carrageenans. In preferred embodiments, the metal salt is a zinc salt (and the antimicrobial composition is referred to as "zinc carrageenate"). Zinc is an inhibitor of such sexually transmitted pathogens as HIV and HSV-2. Zinc acetate and zinc sulfate have been shown to inhibit HIV infection in cell culture, and HSV-2 in both cell culture and laboratory animals. Zinc salts have been shown to be effective in blocking infection by HIV in vitro[39], foot-and-mouth virus, human rhinovirus, influenza A and B, semliki forest virus and sindbis virus[40]. Haraguchi, et al.[39] found that zinc chloride, cadmium acetate and mercury chloride inhibited HIV-1 production as assayed by p24 ELISA and RT. Zinc chloride did not exhibit significant cytotoxicity when present in concentrations of up to 550 µg/mL.

Water-soluble zinc salts useful in the present invention include both inorganic salts and organic salts that exhibit anti-microbial properties without causing unacceptable irritation when used in accordance with the present invention. Preferred water-soluble zinc salts include zinc acetate, zinc propionate, zinc butyrate, zinc formate, zinc gluconate, zinc glycerate, zinc glycolate, zinc lactate, zinc sulfate, zinc chloride, and zinc bromide. $ZnSO_4$, $ZnCl_2$, $ZnBr_2$, $Zn(Ac)_2$, etc. Copper and silver counterpart salts are also useful in the present invention provided that they are non-irritating in vivo and do not cause degradation to any absorbable by-products detrimental to humans. The compositions of this invention will thus include between about 0.03% and 1.5% of the water-soluble metal salts, preferably from about 0.3% to 1.0%. The anti-microbial activity of the composition is greater than a formulation containing the carrageenans as the only anti-microbial agent. In embodiments of the present invention with specific zinc salts, there is a significant increase in antimicrobial activity Without intended to be bound by any particular theory of operation, it is believed that the anti-microbial activity of the formulation is enhanced because the rate at which the metal salt is absorbed by the body is relatively controlled and at the same time, the irritation of the metal salt is reduced.

The complexes of the present invention may be prepared by standard processes whereby the metal ions replace cations that are naturally present on the backbone of the polysaccharide. For example, zinc carrageenan (which refers to a complex between zinc cations and the carrageenans of the present invention) is a compound synthesized by a procedure whereby zinc (II) is non-covalently attached to the sulfate groups of the carrageenans. Carrageenan is a polysaccharide consisting of repeating D-galactose and 3,6-anhydro D-galactose units arranged in a linear fashion. The polymer is highly sulfated having 3 $SO_3$ groups per each disaccharide unit. The binding of zinc to the carrageenans is accomplished by a chemical process developed to replace sodium bound to native carrageenan with zinc. An aqueous solution of a highly soluble zinc salt (such as zinc acetate) is used in this process as a source of zinc cations. The carrageenans are dialyzed against a concentrated solution of zinc acetate allowing positively charged zinc ions to diffuse and complex with the negative sulfate groups of the carrageenans. Excess of zinc is then removed by dialysis against water.

The inclusion of a complex of zinc II metal cations with the carrageenans in the present invention can be achieved by the use of zinc II carrageenate. Zinc carrageenate is synthesized by substitution of the natural carrageenan cations (sodium, potassium, calcium) by zinc cations. Zinc carrageenate is traditionally prepared by dialysis of a solution of carrageenan against a concentrated solution of zinc II acetate. Excess zinc cations are then removed by dialysis against water, before concentrating, and for example, freeze drying. The use of zinc II carrageenate can avoid the use of anions such as lactate or acetate in the present invention.

Another process entails (a) soaking the carrageenans in about a 2.5% zinc lactate (or other suitable soluble zinc salt) in 50:50 alcohol:water liquor for two hours, (b) separated, and (c) washed with alcohol before drying. Steps (a) through (c) may need to be repeated several times to achieve the desired metal content in the carrageenans. Two cycles are normally required to achieve over 50% zinc carrageenan on an equivalent basis.

The above procedures generate a compound, which is water soluble and active against enveloped viruses such as HIV and HSV-2. Unlike inorganic or simple organic zinc salts, zinc carrageenan maintains the preferred rheological properties and possesses a high molecular weight (up to 2,000,000 Da) making it amenable to be formulated into a vaginal product, which is non-irritating and not absorbed. The composition is referred to as a "complex" due to the presence of molecular interactions between the metal and the carrageenans that disfavor or discourage its dissociation to free metal cations. The present complexes of a metal salt and a negatively charged sulfated-polysaccharide complex are distinct from mixtures of water-soluble metal salts and carrageenans in terms of their physical, chemical and/or anti-microbial properties In another aspect of the present invention, applicants have discovered that a combination of the complex between a water insoluble metal salt and carrageenans along with specific antiretroviral agents provides unexpected advantages and synergistic properties. Most particularly, this particular combination of ingredients has been found to provide unexpected results in terms of inhibition of sexually transmitted infections and particularly in blocking vaginal SHIV-RT infections (simian/human immunodeficiency virus-reverse transcriptase). Antiretroviral agents are drugs used for the treatment of infection by retroviruses, primarily HIV. There are a number of different classes of antiretroviral drugs which act at different stages of the HIV life cycle, and these include, for example, non-nucleoside reverse transcriptase inhibitors (NNRTIs), nucleoside reverse transcriptase inhibitors (NRTIs), integrase inhibitors, fusion inhibitors, and CCR5 antagonists.

NNRTIs are compounds which attach themselves to reverse transcriptase and prevent the enzyme from converting RNA to DNA so that HIV's genetic material cannot be incorporated into the healthy genetic material of cells and the cells can be prevented from producing new viruses. These include drugs such as nevirapine, delavirdine, efavirenz, etravirine, MIV-150, MIV-160, MIV-170, dapivirine (TMC-120), and UC-781. Most preferably the NNRTI would be MIV-150, an NNRTI developed by Medivir for use as an antiviral therapeutic. MIV-150 is a tight-bonding HIV-RT enzyme inhibitor characterized by a rapid formation and slow dissociation rate that is effective at inactivating chemical isolates of HIV at very low concentrations. In a preferred embodiment of the present invention, applicants have thus discovered that the specific combination of the carrageenans of this invention with water-soluble metal salts, preferably such as zinc, as well as the NNRTIs such as MIV-150, are effective in totally blocking vaginal SHIV-RT infection. Furthermore, this specific combination has been found to be significantly more effective than the individual combination of the carrageenans with water-soluble metal salts such as zinc; or the carrageenans with NNRTIs, or the carrageenans themselves. In a preferred embodiment, the combination of the carrageenans of the present invention, the water-soluble metal salts, and the NNRTI preferably include the carrageenans discussed above, including lambda carrageenan in amounts of at least about 50% by dry weight of the carrageenans with the remainder of the carrageenans being at least one non-lambda carrageenan, and most preferably a combination of 95% lambda carrageenan and 5% kappa carrageenan, with the overall composition in the form of a gel including between 1% and 5% carrageenan, preferably about 3% carrageenan; the compositions include the water-soluble metal salts preferably comprising zinc salts, most preferably in the form of zinc acetate or zinc lactate, including from about 0.1 wt. % and 1.5 wt. % of the metal, such as zinc, in the overall composition, most preferably about 0.3 wt. % thereof; and include the NNRTIs, most preferably MIV-150, in amounts of from between 5 μM to 5,000 μM (or 0.000185% to 0.185%), and preferably from between 10 μM and 250 μM (or 0.00074% to 0.00925%) of the NNRTI, such as MIV-150, most preferably about 50 μM (or 0.00185%) of the MIV-150.

NRTIs are compounds which are incorporated into the DNA of the virus to stop the building process. They thus result in incomplete DNA that cannot create a new virus. These include drugs such as abacavir, tenofovir and zidovudine.

It has been found by applicants that the NNRTIs and the NRTIs exhibit specific unexpected properties when used in the compositions of the present invention.

In another aspect of the present invention, lignosulfonic acid ("LSA") is combined with a lambda carrageenan or the carrageenans (referred to herein as LSA-carrageenan), to achieve an enhanced anti-microbial effect. LSA is commercially used as an industrial stabilizer, dispersing agent, and strengthener. It is also used as a source of bulk-fiber in cattle feed, and as an emulsifying and dispersing agent in processing certain foods for human consumption. It exists in the cell walls of higher plants. The cell wall fibers are generally made of the polysaccharide, cellulose, the most abundant polysaccharide on earth. In addition to cellulose, the secondary cell wall contains another very abundant material called lignin which is the polysaccharide that makes plants stiffer. By cooking wood chips in a solution of calcium bisulphate under heat and pressure, lignin is converted to a water soluble lignosulfonic acid (LSA) solution known as spent sulfite liquor[31,32]. It is a low molar mass compound with an average molecular weight of approximately 5000 Daltons. Because lignins are very complex natural polymers with many random couplings, the exact chemical structure is not known, but it is considered to be that of a sulphonated polymer in which the basic unit is a propylbenzene structure similar to that of coniferyl alcohol[31]. The usefulness of commercial lignosulfonate comes from its dispersing, binding, complexing and emulsifying properties. The aromatic ring structure of lignosulfonic acid confers on plants the ability to resist attacks from microbes. LSA has been shown to have in vitro anti-HIV activity.

Formulations comprising the carrageenans and LSA can be prepared by adding LSA to the carrageenans, generally in an LSA-total carrageenan weight ratio of from about 20:1 to about 1:20. As in the case of compositions containing a metal salt, a solid buffer salt can be mixed with the carrageenans, usually in a weight ratio of from about 1:1 to about 10:1. The resultant mixture is then solubilized in an aqueous solution. The pH of the carrageenan-LSA formulation may then be adjusted to be from about 6.0 to about 8.0 by adding an acid such as HCl, or a base such as NaOH. LSA in aqueous solutions yields a tan to brown coloration. The intensity of which increases proportionally with the concentration used. Thus, a whitening agent such as titanium dioxide may be included in the composition. In general, the whitening agent is present in an amount of about 0.1 to about 3.0% based on total weight of the composition. The whitening agent may also contribute to the antimicrobial effect.

Without intending to be bound by any particular theory of operation, it is believed that aside whatever anti-viral activity LSA exerts on its own, LSA also functions as a dispersing agent for the carrageenans, and disentangles and elongates them, thus creating greater density of this material and greater anti-microbial potency. On the other hand, the carrageenans provide the preferred rheological properties necessary for acceptable and effective vaginal (and even rectal) administration, which cannot be achieved by LSA in and of itself because it is rather watery in nature. In some embodiments, the combination of the carrageenans and LSA acts synergistically in preventing or inhibiting sexually transmitted infections.

Compositions of the present invention may also contain a vaginally administrable drug in the aqueous formulation along with the pH controlling agent and the lambda carrageenan or the carrageenans. Preferred drugs are contraceptive agents, such as steroid hormones, disclosed in Saleh, et al., U.S. Pat. No. 5,972,372 ("Saleh"), the disclosure of which is hereby incorporated by reference. Examples of contraceptive agents useful in the present invention include progestins, ACTH, androgens, estrogens, gonadotropin, human growth hormone, menotropins, progesterone, progestins (e.g., levonorgestrel, norethindrone, 3-keto-desogestrel and gestodene), progestogen, urofollitropin, vasopressin and combinations thereof. Preferred agents include progestational compounds (e.g., norethindrone acetate and NESTORONE™ ("NES")). (i.e., 16-methylene-17.alpha.-acetoxy-19-norpregnene-3,20-dione)), and progestins (e.g., levonorgestrel (LNG)).

A preferred contraceptive agent is Nestorone 16-methylene-17α-acetoxy-19-norpregn-4-ene-3,20-dione (hereinafter "NES"), which has been identified in the literature as "ST-1435". In comparative studies using the classic bioassay of measuring progestational potency, NES was found to have progestational activity 100 times higher than that of progesterone and 10 times higher than that of levonorgestrel[53]. Therefore, smaller amounts of NES are required to achieve ovulation inhibition. This potency combined with a lack of androgenic, estrogenic and glucocorticoid-like (hepatic glycogen deposition) activity and the lack of effects on lipid or clinical chemistry parameters, confer special advantages for the use of NES in contraceptives[53-55]. However, NES has been shown to undergo rapid metabolism and inactivation upon oral administration making it suitable for use in nursing women when given via implants or vaginal rings[56,57]. A preferred delivery dose of NES when combined with the K/λ carrageenan mixture in gel form is between about 75 and about 100 μg per day, which will reach plasma levels of NES around 200 μmol/L and achieve good bleeding patterns during menus. Other preferred vaginally administrable drugs include agents for hormone replacement therapy such as estrogenic substances (e.g., ethynylestradiol) and other steroidal compounds.

Without intending to be bound by any particular theory of operation, it is believed that the carrageenans possess a dual function of imparting microbicidal properties while providing a prolonged release delivery system for a contraceptive agent or agent for hormone replacement therapy, thus enhancing the activity of the agent.

Any of the compositions described herein may further contain at least one physiologically inert ingredient, such as a physiologically acceptable preservative. Preservatives include alkyl esters of para-hydroxybenzoic acid, such as methyl paraoxybenzoate, propyl paraoxybenzoate, hydantoin derivatives, parabens, such as methyl paraben, propionate salts, triclosan tricarbanilide, tea tree oil, alcohols, farnesol, farnesol acetate, hexachlorophene and quaternary ammonium salts, such as benzolconjure, zinc and aluminum salts, sodium benzoate, benzyl alcohol, benzalkonium chloride and chlorobutanol. In general, the preservative is present in an amount up to about 0.3% based on the total weight of the composition. In addition to inhibiting the growth of microorganisms that may be introduced inadvertently during manufacturing, the preservative prevents any deleterious effects that might occur to the active agents in the composition due to the presence of normal body flora once the composition is introduced into the body. This will prolong the length of time that the active agents in the composition remain active.

In preferred embodiments, the compositions of the present invention e.g., containing the carrageenans as the sole antimicrobial agent, with or without a vaginally administrable drug, and the compositions that contain an additional antimicrobial agent such as the cationic metal salt or LSA, are administered vaginally. The present invention also includes rectal administration. The compositions may be suitably formulated e.g., into gels, creams, foams, films and suppositories, in accordance with standard techniques in the pharmaceutical industry. Gels are preferred. The formulations are preferably administered prior to sexual activity such as intercourse, usually within about one hour before such time. The application of the carrageenan-based formulation in human prevents or inhibits transmission of a sexually transmitted infection (STI), such as *Neisseria gonorrhoeae*, human papillomavirus, HSV-2 and HIV.

Yet another aspect of the present invention is directed to a method for refining a non-absorbable, carrageenan. The formulation is typically prepared by mixing a solid buffer salt and lambda carrageenan, or the carrageenan mixture, in a weight ratio of from about 1:1 to about 10:1. The mixture of solid buffer salt and carrageenan is then solubilized in water or in an aqueous solution, to make the formulation. The pH of the formulation is then adjusted to be from about 6.0 to about 8.0. This is typically achieved by the addition of an acid, such as HCl or a base, such as NaOH. In general, the viscosity of the formulation is from about 20,000 to about 100,000 CPS, preferably from about 30,000 to about 35,000 CPS. At least one physiologically acceptable preservative can be added to the formulation. Examples of such preservatives are disclosed herein. The preservative can be present in the proportions indicated in the various pharmacopoeias, and in particular in a weight ration to the carrageenans of from about 80:1 to about 10:1, preferably from 40:1 to about 15:1.

Solid buffer salts include solid alkaline metal salts of acetic acid, citric acid, phosphoric acid, and lactic acid. In the case of phosphoric acid, the solid alkaline metal phosphate buffer includes solid mixture of tri-basic and di-basic alkali salts of phosphate, preferably in anhydrous form, wherein alkaline metal includes, but is not limited to, potassium and sodium. Any physiologically acceptable buffer can be used. However, in the case where water-soluble zinc salts are utilized, the phosphates are less preferred, and in these formulations, the acetates, citrates and lactates are more preferred. In preferred embodiments, these buffer solutions comprise mixtures of acetic acid and sodium acetate; citric acid and sodium citrate; and lactic acid and sodium lactate.

Without intending to be bound by any particular theory of operation, it is believed that the carrageenans are dry powders that are extremely hydroscopic when exposed to the atmosphere. The uptake of atmospheric moisture into the dry ingredient causes clumping of the material. The problem compounded when the material is then introduced into the aqueous base solution, such that complete incorporation of the carrageenans into a homogeneous aqueous solution cannot be obtained. It is also believed that by mixing the carrageenans and at least one solid buffer salt together, the solid buffer salt absorbs the atmospheric moisture that the carrageenans would have absorbed when exposed to the atmosphere, thus preventing or substantially reducing clumping of the carrageenans. It is further believed that the process serves to increase the solubility of carrageenans in water, and achieves stabilization of the pH.

The following examples are intended to further illustrate certain embodiments of the invention and are not intended to limit the invention in any way.

Example 1

Production of 500 Liters of the Carrageenans

In preparing the lambda carrageenan or the carrageenan mixture, (1) the formulation ingredients should be weighed individually in a clean, dry weighing vessel; (2) the ingredient's "actual" weight, not protocol weight, should be recorded in the manufacturing production log regardless of even slight variation between the two; (3) any bulk ingredient container containing an artifact(s) or contaminate should not be used and the container should be closed, sealed, marked "CONTAMINATED" and removed from production area; (4) in process production batch should not be transferred from one vessel to another before manufacturing is completed and formulation has passed quality control testing; and (5) production vessel should remain closed during manufacturing to avoid loss of water due to evaporation, especially during any steps that require heating.

Additionally, carrageenan has proven to be stable in the solid state and the production state under a variety of adverse conditions, including freezing or autoclaving, for 24 months.

The following pertains to a procedure for that was used to make a formulation containing a carrageenan mixture of lambda (λ) and kappa-II (K-II) carrageenans (the (K-II/λ carrageenan mixture). In the course of preparing the K-II/λ carrageenan mixture from 100 mL laboratory size batches on to scale-up of 15 and 30 liter laboratory batches to finalizing the manufacturing procedure of 500 liter batches, it became difficult to obtain batch-to-batch consistency of the desired formulation. The present method surprisingly overcame these difficulties and produced formulations of the K-II/λ carrageenan mixtures having consistent batch-to-batch quality.

Equipment:

Production Vessel—IKA, EMA 9/500AIUTL, is a water jacket production vessel that allows for rapid heating and cooling of solution during production.

Ingredients:

the K-II/λ carrageenan mixture;

Phosphate buffer saline (PBS) [containing: NaCl—120 mmol/L, KCl—2.7 mmol/L, Phosphate buffer (potassium phosphate monobasic and sodium phosphate dibasic)—10 mmol/L—(Sigma Aldrich, Saint Louis Mo.);

p-Hydroxybenzoic methyl ester (Methyl paraben)—(Nipa Laboratories, Pontypridd, UK);

Hydrochloric Acid (HCl)—Merck, Darmstadt, Germany;

Purified water—Clean Chemical Sweden AB, Borlange, Sweden.

Procedure (1). Weighed ingredients in the following quantities:

| INGREDIENT | QUANTITY |
| --- | --- |
| Purified water (3 Parts) | 484.0 kg |
| the K-II/λ carrageenan mixture | 15.0 kg |
| Phosphate buffer saline (PBS) | 4.8 kg |
| Methyl paraben | 0.5 kg |
| Hydrochloric acid (10%) | 0.5 kg |

(2). Carefully and thoroughly mixed the dry ingredients, the K/λ carrageenan mixture and Phosphate buffer saline (PBS) together;

(3). Inspected production vessel to ensure that mixing chamber is clean, dry and free of artifacts, and that the bottom value is closed;

(4). Filled the production vessel with 100.0 L (Part I) of purified water and began stirring:

turbin 500 rpm and anchor 20 rpm. Water is added in 3 parts. The first part was enough to dissolve the methyl paraben. The second part aided in reducing the temperature, sufficiently diluted the HCl so acidic hydrolysis of carrageenan did not occur while maintaining low enough solution level so when adding the carrageenan/PBS mixture, the delivery sieve could be lowered into the mixing vessel such that it did not come into, contact with the base solution and was lower than the vessel access hatch so the excessive 'dusting' of the mixture was not lost. The third part completed the final concentration.

(5). Continued stirring and add 0.5 kg of methyl paraben and 0.5 kg of HCl. Closed vessel access hatch and heat water 75° to 85° C. Once this temperature was reached, we continued stirring for a minimum of 10 minutes to dissolve methyl paraben.

(6). Discontinued heating and add 250.0 kg (Part II) of purified water. Cooled solution to 25° to 30° C. The addition of the water expedited the cooling process. The solution needed to be cooled so that it was not producing steam when the next addition of ingredients was made. Besides preventing water loss when the vessel was open for the next addition, steam caused the carrageenan/PBS mixture to clump and stick to the sieve that was used in the addition;

(7). Opened access hatch and began the addition of carrageenan/PBS mixture slowly through a sieve with gentle shaking. Addition took approximately 20 minutes. Coincided the addition of the mixture with increasing the stirring speed to a maximum speed of turbin 1200 rpm and anchor 20 rpm. The viscosity of the solution increased exponentially with the addition of the carrageenans. If the stirring speed was not significant, the carrageenan formed 'hydro-sealed' clumps, which never became dissolved and incorporated into the solution, thereby rendering the batch unacceptable. ('Hydro-sealed' clumps are pockets of dry carrageenan, which are surrounded with an outside coating of semi-hydrated carrageenan, which become impenetrable to water due to carrageenan's extremely large molecular weight and flexible structure.);

(8). Closed access hatch and continued stirring at maximum speed, turbin 1200 rpm and anchor 20 rpm. Added 134.0 kg purified water (Part III) and disconnect the waterline, close value. Heated solution to 75° to 80° C. by applying 52% heat; and (9). Checked that all the values were closed and applied the vacuum to the vessel at 400 mbar. Stirred solution at slightly reduced speed, turbin 1100 rpm and anchor 20 rpm, under vacuum for 1.5 hr at 75° to 80° C. The constant stirring of the solution, which was necessary for even distribution and complete incorporation of ingredients, caused excessive air entrapment. The vacuum pulled this air out of the solution;

(10). Turned heating OFF, stirring OFF, and vacuum OFF. Removed Testing Sample from production vessel and tested for Control Test #1 Completed incorporation and even distribution;

Control Test #1: Complete Incorporation and Even Distribution

Removed approximately 90 μL of the in-process mixture (used a large orifice 200 μL pipette tip to aid in removing the carrageenan solution) and mixed in 10 μL of a 0.1% methyl blue TS (1:1, isopropyl alcohol:dH2O) in a 500 μL Eppendorff tube. The mixture in the tube should appear as an even blue color. This indicates that the K-II/λ carrageenan mixture is evenly distributed within the solution. Prepared a microscope slide with a 10 μL of this mixture; covered with a cover slip and viewed under low magnification (10×). The K-II/λ carrageenan mixture should appear as large purple strands. This indicates that the K-II/λ carrageenan mixture was completely incorporated and the solution is "PASS". If the strands are blue or large blue clumps are visible, then the K-II/λ carrageenan mixture is not completely incorporated and solution is "FAIL". Continued processing the solution under the conditions of step #9. Rechecked solution at 0.5 hour intervals until solution is "PASS".

(11). When the solution is "PASS" for Control Test #1, test for Control Test #2, pH;

Control Test #2: pH

The testing sample should be cooled to 25° C.±2 (a range of 23° C. to 27° C.) for testing. The pH should be 7.0±0.1 (a range of 6.9 to 7.1). This indicates that the solution's pH is uniform and the solution is "PASS". If the solution is not within the acceptable pH range (6.9 to 7.1) the solution is "FAIL". If the solution is "FAIL", the solution needs to be adjusted, as needed with either 10% HCl (to decrease the pH) or 1N NaOH (to increase the pH) in 25 mL increments until the solution is "PASS". With each incremental addition of either acid or base, thorough stirring (stirring and vacuum condition step #9, no added heat) is needed to ensure even distribution throughout batch before re-testing the pH. Recheck solution after stirring/vacuum for 0.5 hour. Continue in this manor until solution is "PASS".

(12). When the solution is "PASS" for Control Test #2, begin cooling the mixture to 25° C.

±2° (23° C. to 27° C.). The stirring speed, which should be OFF at this point, will need to be increased as the solution thickens upon cooling. At start, turbin OFF and anchor 20 rpm, increase turbin 20 rpm/15 mm and increase anchor 10 rpm/30 mm, ending with turbin 1000 rpm and anchor 40 rpm. It is preferred not to increase stirring to rapidly; otherwise, air entrapment may result. If this should happen, apply the vacuum 400 mbar until solution is free of air bubbles;

(13). Remove Final Testing Sample from the production vessel and retest for Control Test #2 pH and for Control Test #3, Viscosity.

Control Test #3: Viscosity

The testing sample should be heated to 35° C.±2° (a range of 33° C. to 37° C.). To optimize performance, the viscosity should be about 30,000 to about 40,000 cP. Viscosity measurements indicate that the solution's viscosity is uniform with the PC Reference sample and CCS production batches and the solution is 'PASS". If the solution is "FAIL" obtain testing samples from the top and the bottom of production vessel and conduct Control Test #2, pH and Control Test #3, Viscosity on each sample. If the solution is still "FAIL", repeat step #9 and step #12 and retest the solution for Control Test 3#, Viscosity. If solution is "FAIL" an Out of Specifications Study shall be undertaken to determine the source of out of specification production.

It was discovered that adjusting viscosity with the addition of water yields an unknown percent/concentration to the final production batch rendering the production batch unacceptable.

(14). When the solution is "PASS" for Control Tests #1, #2, and #3 it is an acceptable production' batch which can be processed for the final control testing. Connect the transfer tube containing a filter bag to the bottom value of the production vessel and transfer the formulation into storage containers. Retain a Test Sample for Microbiological Testing before filling applicators.

The final formulation prepared in the process discussed above has the following components.

| Weight/Percent: 500 Liters of formulation | | |
| --- | --- | --- |
| Component | Weight | Percent |
| Purified Water | 484.0 kg | 96.8 |
| Methyl paraben | 500 g | 0.1 |
| PBS: | | |
| NaCl | 120 mmol/L | |
| KCl | 2.7 mmol/L | |
| Phosphate salts | 10 mmol/L | |
| 10% HCl | 500 g | 0.1 |
| the K-II/λ carrageenan mixture | 15 kg | 3.0 |

The final formulation has a pH of about 7.0 which was adjusted by adding HCl solution and 1:1 ratio of $K_3PO_4$ and $Na_2HPO_4$.

Example 2

Effect of Carrageenan on HIV Infections In Vitro

Carrageenan has been shown to block HIV and other enveloped viruses by several laboratories including the laboratory of the PI[15-19]. Several different types of target cells and strains of HIV have been employed in these studies. Generally, 50% blocking is observed at a few micrograms/mL. This result is similar to other sulfated polysaccharides such as heparin and dextran sulfate.

Example 3

Intra-Vaginal Viral Infection Studies

HSV-2/Mouse

The HSV-2/mouse (Balb/C) system is widely utilized by most investigatory groups engaged in the development of a microbicide. An important difference between the system established by Phillips[20-22] and other systems is the utilization of viral dose range comparison. The standard viral challenge dose, 100% infection dose or $10^4$ pfu, used by others for evaluation of a microbicide is rate limiting. The large majority of the microbicides under development, as well as many of the OTC spermicides will show a significant rate of protection against HSV-2 infection at this viral challenge doses. However, Phillips has utilized a virus concentration method that will enable evaluation at viral challenge doses of $10^5$, $10^6$, and 1,000×100% infection dose.

Using this viral challenge dose system, a comparison study was conducted to evaluate the comparison protection rates of a number of microbicides under development, OTC spermicides and lubricants, and possible formulations for use as a placebo in the clinical trials to evaluate efficacy of a microbicide. In addition to a composition of the present invention containing the K-II/λ carrageenan mixture (also referred to herein as the "K/λ carrageenan composition"), comparative test formulations were: microbicides under development such as BufferGel™ and No Fertil, OTC spermicides: K-Y Plus® Gynol II®, and Advantage S™; OTC vaginal lubricants: Replens® and K-Y Jelly®; and possible placebo formulations: 2.5% Carbopol® and 2.5% methyl cellulose.

Test formulations fell into three categories with respect to efficacy in protecting mice from vaginal HSV-2 infection. At the viral challenge dose of $10^4$ pfu, with the exception of K-Y Jelly, Carbopol and methyl cellulose, all formulations provided a significant level of protection against infection from HSV-2. However, at the viral challenge dose of $10^5$, with the exception of the K-II/λ carrageenan composition, all formulations only provided a minimum level of protection. The K-II/λ carrageenan composition was the only formulation still affording a level of protection against viral infection at the viral challenge dose of $10^6$ pfu[20] By evaluating various formulations in the viral dose range comparison system the resulting data was the first demonstration of the unexpected high level of protection against viral infection that the K-II/λ composition provides.

Therefore, it can be concluded that the HSV-2/mouse system can be employed as a means by which candidate microbicides can be evaluated and compared under the same testing conditions to identify potential effective microbicides.

Example 4

Duration of Activity—HSV-2/Mouse

One of the criteria set forth by UNAIDS (World Health Organization, AIDS branch) for an ideal microbicide states 'it should be active upon insertion and for a long period of time,' giving a woman more flexibility in product use. Additionally, the time course for infection by cell-free or cell-associated HIV to occur may not be immediate. The HSV-2/mouse system can be employed to evaluate the duration of time that a microbicide would retain activity. This is done by intra-vaginal application of a test formulation, waiting a set period of time, and then challenging mice with a known dose of virus. "Duration of activity" testing was conducted using Gynol II (a 2% N-9 containing OTC spermicide), BufferGel® (a low pH microbicide under development) and the K-II/λ carrageenan composition, at five minutes and 1.5, 3, 6 and 18 hours following formulation application. By the 1½-hour time point, Gynol II® no longer afforded any protection against infection and BufferGel® had dropped to being only 30% effective. BufferGel's efficacy continued to drop over time and no longer afforded any protection by 6 hours. In marked contrast, the K-II/λ carrageenan composition remained 85-100% effective in protecting against HSV-2 infection up to 6 hrs and remained 72% effective at 18 hrs. The K-II/λ carrageenan composition continued to retain some level of activity for up to 24 hours. See FIG. 1. The extended duration of protection from viral infection is unique to carrageenan, in particular K-II/λ carrageenan composition.

Example 5

Intra-Rectal Viral Infection Studies—HSV-2/Mouse

Ideally, a microbicide that was effective in protecting against infection by HIV could be used rectally as well as vaginally. Using an intra-rectal viral challenge modification of the HSV-2-/mouse system an evaluation of the efficacy and safety of a microbicide was explored.

Pre-treatment of the rectum with the K-II/λ carrageenan composition significantly reduced the number of animals that became infected following rectal challenge with HSV-2, compared to pretreatment with PBS or methylcellulose (an inert placebo)[23]

Example 6

Effect of K-II/λ Carrageenan Composition on Vaginal Flora

It is important that the use of a microbicide does not disrupt the balance of the natural vaginal flora. In vitro studies indicated that carrageenan did not enhance or inhibit the growth rate of *Lactobacillus acidophilus*, the most common bacterium present in the vaginal flora. A study conducted in 35 women participating in a Phase I clinical trial for the vaginal safety of the K-II/λ carrageenan composition showed no significant change in vaginal flora, as measured by the presence or absence of bacterial vaginosis[13].

Example 7

HIV/Mouse Viral Transport System

Although mice can not be infected with HIV, it has been shown that when active or inactivated virus is instilled into the vagina of mice, virus can be subsequently detected in the lymph lodes by the use of reverse transcriptase polymerase chain reaction (RT-PCR)[24] Evidence has been presented that dendritic cells played a role in the uptake of virus and subsequent transport to the lymph nodes. This conclusion is in agreement with studies implicating dendritic cells in the initial stage of sexual transmission of HIV[25].

Results indicate that the K-II/λ carrageenan composition is efficacious in preventing HIV from reaching the lymph node, presumably by blocking HIV transport from the vagina via dendritic cells.

HIV transport using a mouse system and Aldrithiol™-2 inactivated virus were used. This is a standard method for inactivating HIV that does not alter the viral envelope. The spleen and the lymph nodes were assayed for the detection of HIV in order to establish the spleen as an alternate repository site for HIV. The spleen (as opposed to the lymph nodes) allows for obtaining relatively larger amounts of RNA for performing RT-PCR for the detection of HIV. In addition, extraction of spleens is less time consuming than removal of the lymph nodes thereby lessening the probability of RNA degradation.

Figure 2:
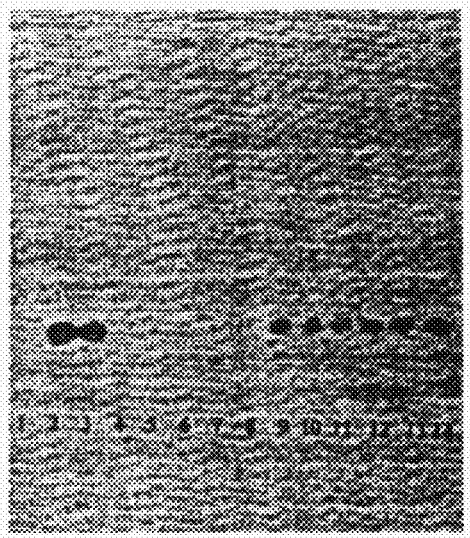
FIG. 2 is a graph of Southern Blot hybridization of RT PCR products from RNA extracted from the spleens. Lane 2 and 3 are positive controls. Lanes 4 to 8 are from mice that were pretreated with a composition containing the carrageenans of the present invention, 5 minutes before viral challenge. Lanes 9 to 14 are from mice inoculated vaginally with HIV.

To determine the efficacy of the K-II/λ carrageenan composition in preventing HIV from crossing the cervical/vaginal barrier, mice were randomized into three groups: 1) non-treated PBS control mice; 2) mice pre-treated with methyl cellulose (inert placebo); and 3) mice pretreated with the K-II/λ carrageenan composition. Results are shown on the Southern Blot in FIG. 2 and the table below.

| Treatment | PT-PCR +/total | Percentage Positive (Infected) |
|---|---|---|
| PB5 | 16/22 | 72% |
| Methyl Cellulose | 7/10 | 70% |
| K-II/λ carrageenan composition | 2/22 | 9% |

Data from PBS (control) and methyl cellulose treated and mice treated with the K-II/λ carrageenan composition show that the K-II/λ carrageenan composition significantly reduced the number of positive (i.e., infected) animals, and that methyl cellulose had no effect as compared to PBS (control). The data also indicate that the K-II/λ carrageenan composition was effective in preventing HIV from leaving the vaginal vault.

Example 8

Cell Trafficking/Mouse System

It has previously been suggested that sexual transmission of HIV could be mediated by HIV-infected lymphocytes or macrophages in semen that cross the genital tract epithelium[26,27]. In order to test the hypothesis that mononuclear blood cells traffic from the vaginal vault through intact epithelia, double-vitally-stained activated mononuclear blood cells (mouse) were placed in the vagina of mice. Four hours later, animals were sacrificed and iliac and inguinal lymph lodes and the spleen were removed and cells were dissociated and count by fluorescence microscopy. Numerous double-stained cells were observed in the iliac and inguinal lymph nodes and the spleen[28,XX]. To evaluate the effect that the carrageenan composition may have on blocking this process, animals were pre-treated with the test formulation prior to instillation of labeled cells.

| Mouse | Inoculation | Inguinal & Iliac Lymph nodes | Spleen |
|---|---|---|---|
| 1 | Macrophages | 36 | 555 |
| 2 | Macrophages | 52 | 366 |
| 3 | Macrophages | 59 | 672 |
| 4 | Macrophages | 87 | 786 |
| 5 | Macrophages | 61 | 357 |
| 6 | Macrophages | 40 | 859 |
| 7 | Macrophages | 54 | 312 |
| 8 | K-II/λ carrageenan + | 4 | 30 |
| 9 | Macrophages | 4 | 6 |
| 10 | K-II/λ carrageenan + | 6 | 48 |
| 11 | Macrophages | 3 | 53 |
| 12 | K-II/λ carrageenan + | 3 | 3 |
| 13 | Macrophages | 14 | 120 |
| 14 | K-II/λ carrageenan + | 27 | 245 |
| 15 | Macrophages | 38 | 96 |
| | K-II/λ carrageenan + Macrophages Methyl cellulose + Macrophages Methyl cellulose + Macrophages Methyl cellulose + Macrophages | | |

Donor's cells were present both in the iliac and inguinal lymph nodes and in the spleen. When mice received only a vaginal inoculation of macrophages, the recipient animals had an average of 55 labeled donor's cells in the draining lymph nodes and of 558 cells in the spleen, respectively. In mice that received a vaginal pre-inoculation of carrageenan composition (indicated in table above as "K-II/λ carrageenan") an average of only 4 cells were counted in the draining lymph nodes, and an average of only 28 were observed in the spleen. The difference between untreated and K-II/λ carrageenan composition-treated animals was significant. When the recipients were pre-inoculated with methyl cellulose, the number of donor's cells that reached lymph nodes and spleen averaged 26 in the lymph nodes and 153 in the spleen. The difference between K-II/λ carrageenan composition-treated mice and methyl cellulose-treated mice was significant, whereas the difference between untreated mice and methyl cellulose pre-inoculated mice was not significant. No fluorescent cells were observed in control mice that had been inoculated with frozen-thawed CMTMR stained macrophages.

Example 9

Microbicide Effect on Papillomavirus

The K-II/λ carrageenan composition has also been proven effective on blocking bovine papillomavirus (BPV) foci formation in vitro (data not shown). The K-II/λ carrageenan composition is efficacious in preventing human papillomavirus (HPV) from transforming human vaginal explants in a xenograft system. The SKID mouse xenograph system employs explants of human vaginal tissue rolled into cylindrical tubes that are grafted subcutaneously on NOD/SKID (immunodeficient) mice[29]. The grafts are allowed to heal for two weeks, at which time one end of the tube is opened and a test compound is instilled followed by HPV challenge. In experiments evaluating the K-II/λ carrageenan composition, in 14 out of 14 saline treated control explants were transformed. In contrast, only 1 out of 17 explants treated with the K-II/λ carrageenan composition was transformed (data not shown).

Example 10

Effects of the K/λ Carrageenan Mixture in Dilution Assay

Figure 11:
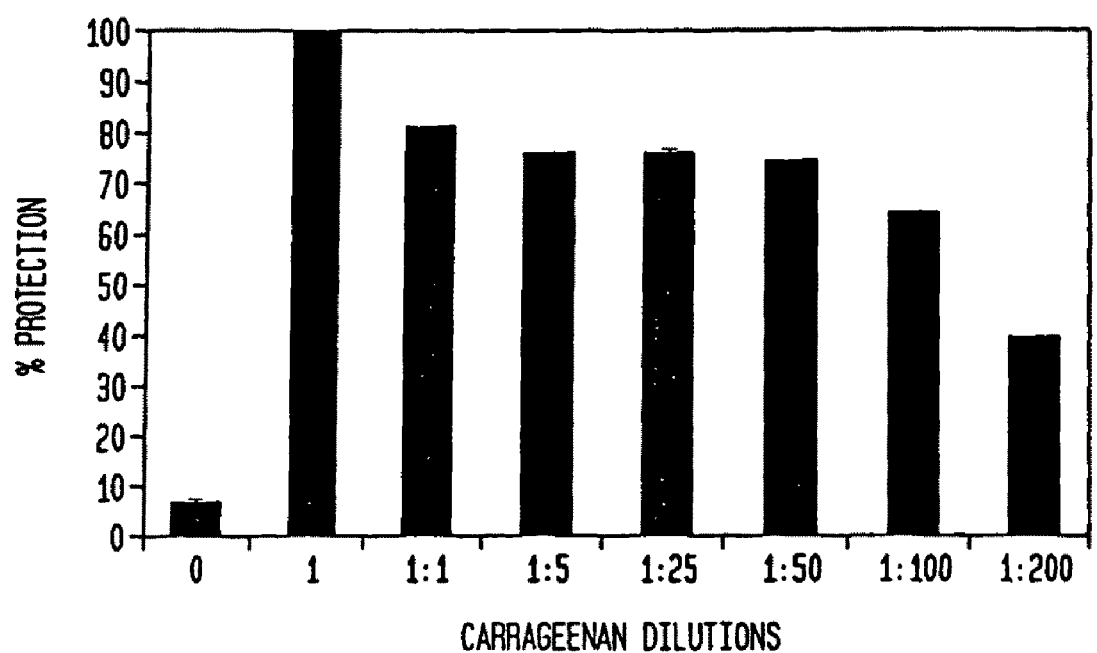
FIG. 11 is a bar graph comparing the effectiveness of various dilutions of carrageenan compositions of the present invention in protecting mice from infection by HSV-2. Results show that even when the carrageenans are diluted 1:200, they still were able to provide 40% protection from infection.

The K/λ carrageenan mixture is also effective at high dilutions as demonstrated in the HSV-2 mouse system. A 3% K-II/λ carrageenan composition was diluted in PBS to make 1:1, 1:5, 1:25, 1:50, 1:100, and 1:200 dilutions. Dilute solutions were vaginal administered to mice followed by $10^4$ (100% infection dose) of HSV-2. The results from these experiments are unexpected. Instead of observing a dose dependent decrease in the anti-viral protection rate the K-II/λ carrageenan composition dilution of 1:50 retained most of the anti-viral protection rate as less dilute solutions. Furthermore, significant activity was retained even with the 1:200 solution. See FIG. 11.

Example 11

Effects of the K-II/λ Carrageenan Composition-Based Formulations Against HIV

Figure 3:
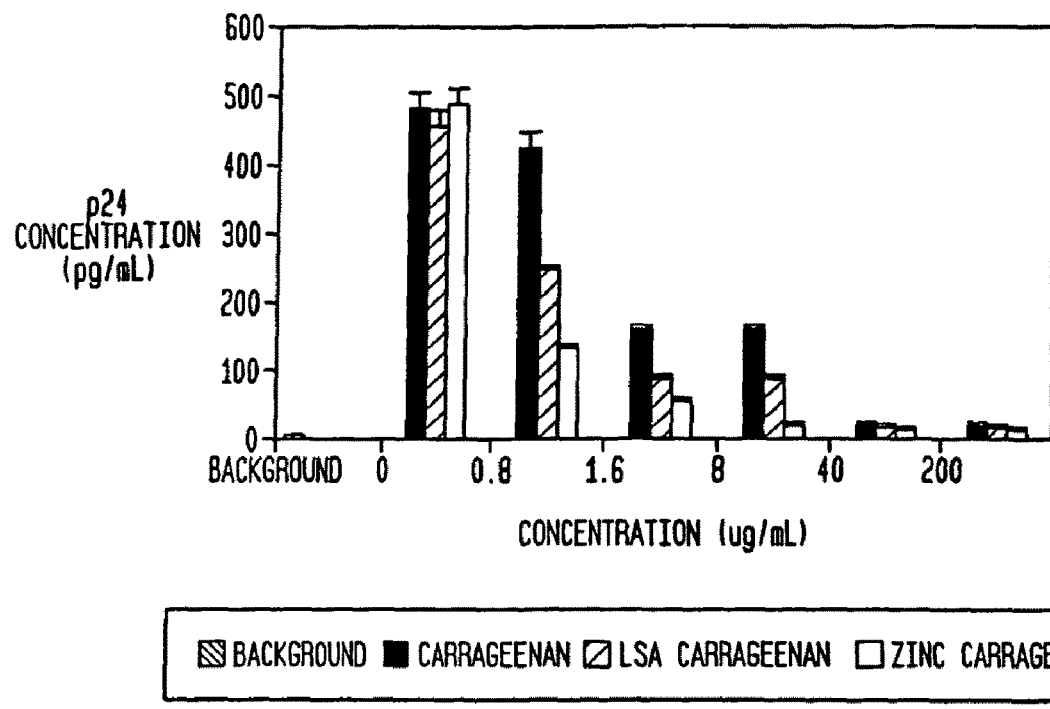
FIG. 3 is a bar graph showing p24 (HIV) concentration versus concentration of a composition containing the carrageenans of the present invention, another composition of the present invention that contains a complex of the carrageenans and a water-soluble zinc salt ("zinc-carrageenan"), and ligno-sulfonic acid (LSA).

Compounds have been identified which when added to, or bound to the carrageenans of the present invention, significantly increase efficacy in blocking HIV infection of PBMCs in vitro. Studies on the effectiveness of Zn-carrageenan and LSA-carrageenan on blocking HIV infection of PBMCs have shown that both formulations are more effective than a compositions containing the carrageenans alone at lower concentrations. The testing results are shown in FIG. 3.

Example 12

Effects of LSA-Carrageenan Against HSV-2

Figure 4:
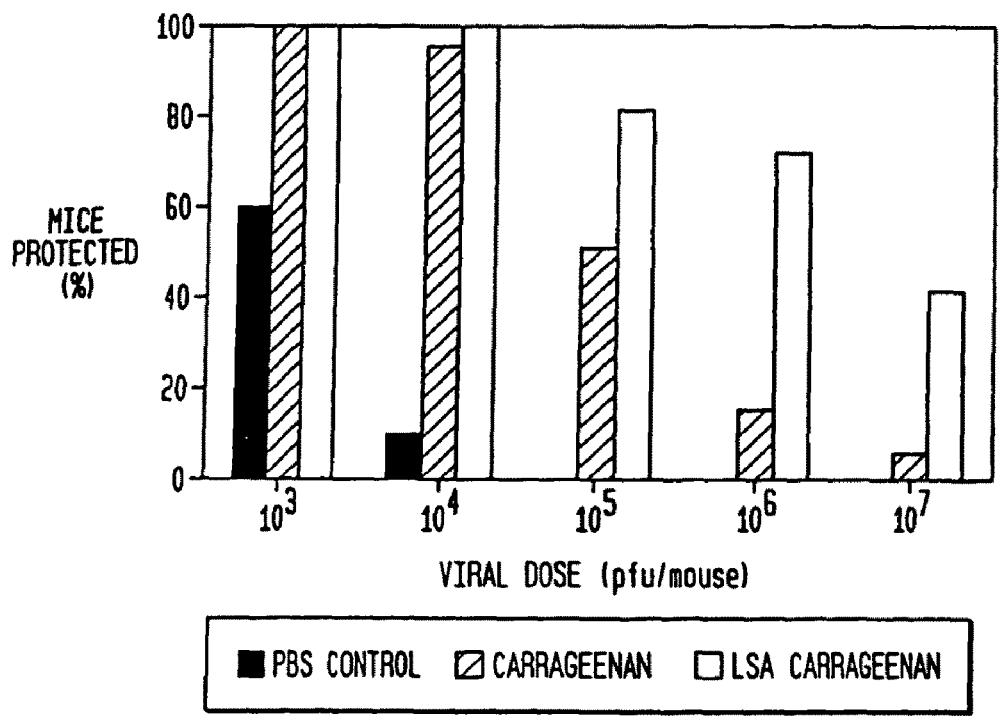
FIG. 4 is a graph showing comparison between a composition of the present invention containing the carrageenans and LSA, and a composition of the present invention containing the carrageenans, in the HSV-2/Mouse system. The results show that the composition containing LSA and the carrageenans is more efficacious than a composition containing the carrageenans alone.

Results indicate that LSA-carrageenan is more efficacious in blocking HIV infection than the carrageenans. (See FIG. 4.) Originally LSA did not seem to be an ideal candidate compound for a microbicide due to the fact of its brown coloration. However, it was found that a concentration of 0.25%, LSA is highly effective and imparts negligible coloration when formulated. In order to ensure that LSA would not impart discoloration, white cotton fabric was soaked overnight in 3% LSA and then rinsed with tap water; the results revealed no change in the color of the fabric. LSA-carrageenan was compared to carrageenan in the HSV-2/mouse system in order to determine efficacy in blocking viral infection in vivo. Preliminary results showed that LSA-carrageenan was more efficacious than carrageenan in blocking viral infection.

In addition to the results presented above, LSA-carrageenan was compared to the K-II/λ carrageenan composition alone at a viral challenge dose of $10^6$ pfu, in three separate experiments. LSA-carrageenan was significantly more effective than the carrageenan composition alone in all experiments. The addition of other sulfated polymers to carrageenan composition did not increase the effectiveness of the formulation. For example, the addition of 5% dextran sulfate or 5% heparin to K-II/λ carrageenan composition had no effect on efficacy against HSV-2 infection in mice.

Evaluation of K-II/λ carrageenan composition (referred to in the three tables below as "Carrageenan") Formulations with and without LSA HSV-2 $10^6$ pfu viral dose is equivalent to 100 times the viral dose that would infect all unprotected mice. It is necessary to use such high doses of virus because carrageenan is extremely effective at inhibiting viral infection.

Each formulation is initially tested in a total of 20 mice. Compounds or formulations that show a blocking effect are assayed again in another 20 mice. The number of mice infected is an average.

| FORMULATION | # MICE INFECTED TOTAL # MICE | % INFECTED |
| --- | --- | --- |
| 3% Carrageenan | 14/20 | 70 |
| 1% Carrageenan | 20/20 | 100 |
| 0.5% Carrageenan | 20/20 | 100 |
| 3% Carrageenan + 3% LSA | 4/20 | 20 |
| 3% Carrageenan + 1% LSA | 2/20 | 10 |
| 3% Carrageenan + 0.5% LSA | 4/20 | 20 |
| 3% Carrageenan + 0.25% LSA | 5/20 | 25 |
| 3% Carrageenan + 0.1% LSA | 7/20 | 35 |

The viral dose is 100 times the 100% infection rate and no compound other than the minimal effect of 3% carrageenan has had any effect at such a high virus dose.

Subsequently, LSA was assayed without Carrageenan to better evaluate its inhibitory properties. LSA was added to the inert thickener, methylcellulose, to maintain the same viscosity that vaginal products (lubricants, spermicides, and microbicides) generally have. (Data shown below.)

Evaluation of LSA without Carrageenan

| FORMULATION | # MICE INFECTED TOTAL # MICE | % INFECTED |
| --- | --- | --- |
| 3% Carrageenan | 14/20 | 70 |
| 3% LSA - methylcellulose | 8/20 | 40 |
| 1% LSA - methylcellulose | 8/20 | 40 |

LSA proved to be more effective than carrageenan, showing better blocking of HSV-2 infection than carrageenan. However, the combination of the two ingredients out-performed either one alone.

Example 13

Use of LSA in Microbicides

Figure 5:
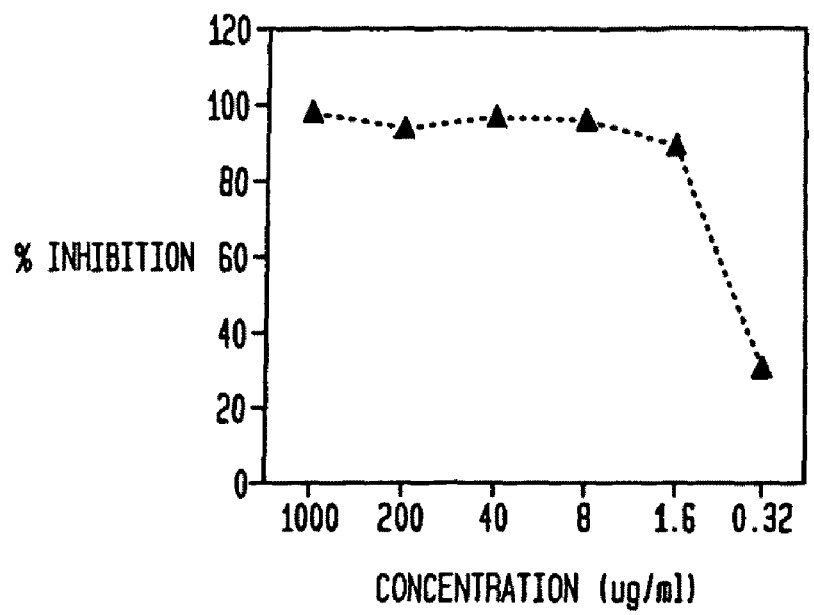
FIG. 5 is a plot of the percent inhibition by LSA of viral replication as measured by p24 ELISA.

LSA is effective as a microbicide against HSV-2 infection, HIV, and other STI's, with or without carrageenan. The sulfated polymer LSA is effective in protecting epithelial cells in vitro against HIV infection and mice from HSV-2 infection. The inhibitory effect may be observed with other enveloped viruses such as the human pathogen, human T cell leukemia virus. In addition, epithelial cells are protected against the human papillomavirus, which is not an enveloped virus. The inhibitory efficaciousness of LSA may thus extend to a broader range of STI's. The testing results are shown in FIG. 5.

Example 14

Effects of Zn-Carrageenan Against HSV-2

Figure 6:
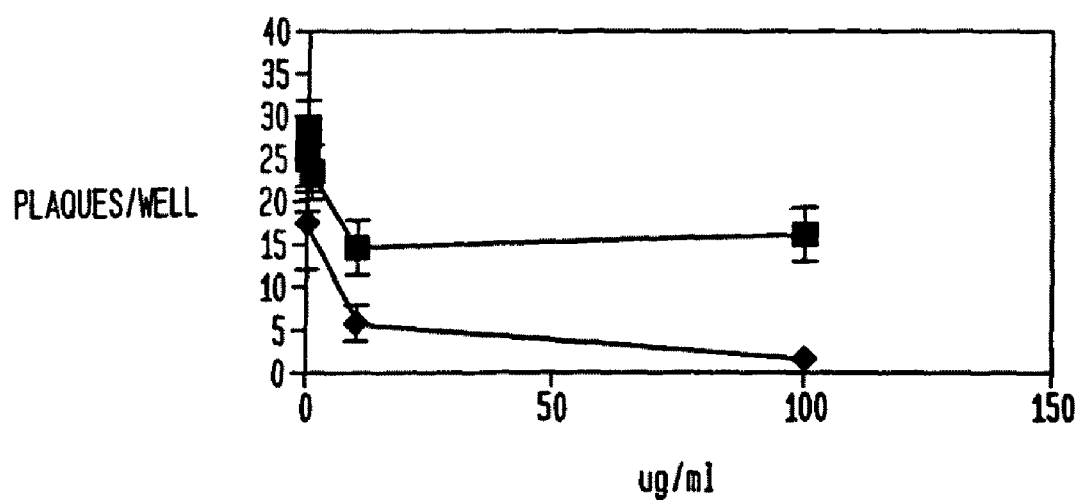
FIG. 6 is a graph of the efficacy of a composition containing the carrageenans of the present invention, and another composition of the present invention that contains zinc-carrageenan, in preventing plaque formation of HSV-2 in Vero cells as a function of dose.

Studies on the effectiveness of Zn-carrageenan against HSV-2 infection have been conducted in vitro and in vivo. In vitro studies assayed the effect of Zn salts alone in preventing plaque formation in the HSV-2 plaque assay[41]. Zn salts were found to have an $IC_{50}$ at a 50 mM concentration in reducing plaque formation. It was observed that Zn-carrageenan is significantly more effective than carrageenan or Zn salts alone in preventing plaque formation $IC_{50}$<10 μg/mL, or <25 mM. The testing results are shown in FIG. 6.

Figure 7:
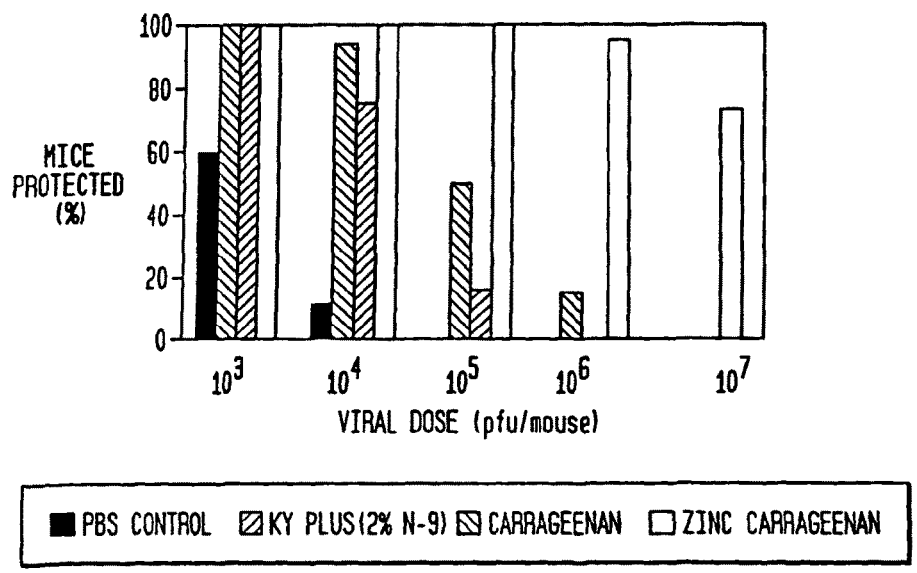
FIG. 7 is a graph showing the efficacy of a composition containing the carrageenans of the present invention, and another composition of the present invention that contains zinc-carrageenan, in protecting mice from infection from HSV-2, following vaginal challenge.

Zn-carrageenan has also been evaluated in the HSV-2/mouse system (see FIG. 7). In order to compare Zn-carrageenan with the OTC spermicide K-Y Plus and the K-II/λ carrageenan composition, HSV-2 viral challenge doses ranging from $10^3$ pfu or 50% infection dose, to $10^7$ pfu or 1,000× 100% infection dose was also used. Applicants had determined that K-II/λ carrageenan composition could protect some animals at a viral challenge dose of $10^6$ pfu or 100× 100% infection dose. No other candidate microbicide tested was able to afford protection at this viral dose. In preliminary studies it has been observed that Zn-carrageenan significantly protect mice against HSV-2 infection at this dose as well as at a viral challenge dose of $10^7$ or 1,000×100% infection dose. The fact that the addition of Zn to the K-II/λ carrageenan composition (to form a complex) increased the level of antiviral protection was most unexpected.

Example 15

Zn-Carrageenan Duration of Activity

Figure 8:
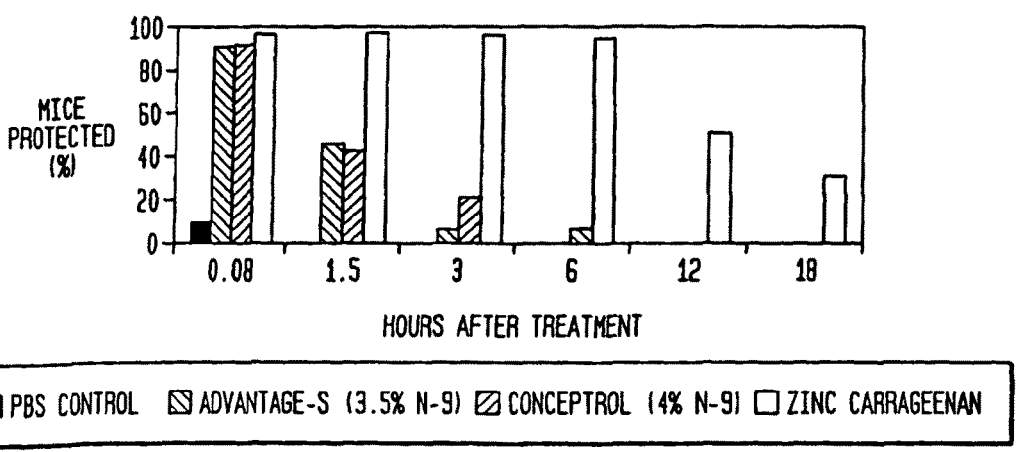
FIG. 8 is a graph showing the comparison of long-term activity of a composition of the present invention containing zinc-carrageenan compared to two known products, Conceptrol and Advantage S, at a viral challenge dose of $10^4$ or 100% infection dose of HSV-2.

The K-II/λ carrageenan composition remains active in the mouse vagina for an extended period of time. Similar experiments were carried out to compare Zn-carrageenan to two OTC spermicides, Advantage S and Conceptrol, for duration of activity. It was observed that Zn-carrageenan did not lose any level of activity in 6 hours, where Advantage S and Conceptrol showed a 50% reduction in activity at 1.5 hours and by 3 hours were no longer able to afford protection (see FIG. 8).

Example 16

Zn-Carrageenan Efficacy Post-Viral Challenge

Figure 9:
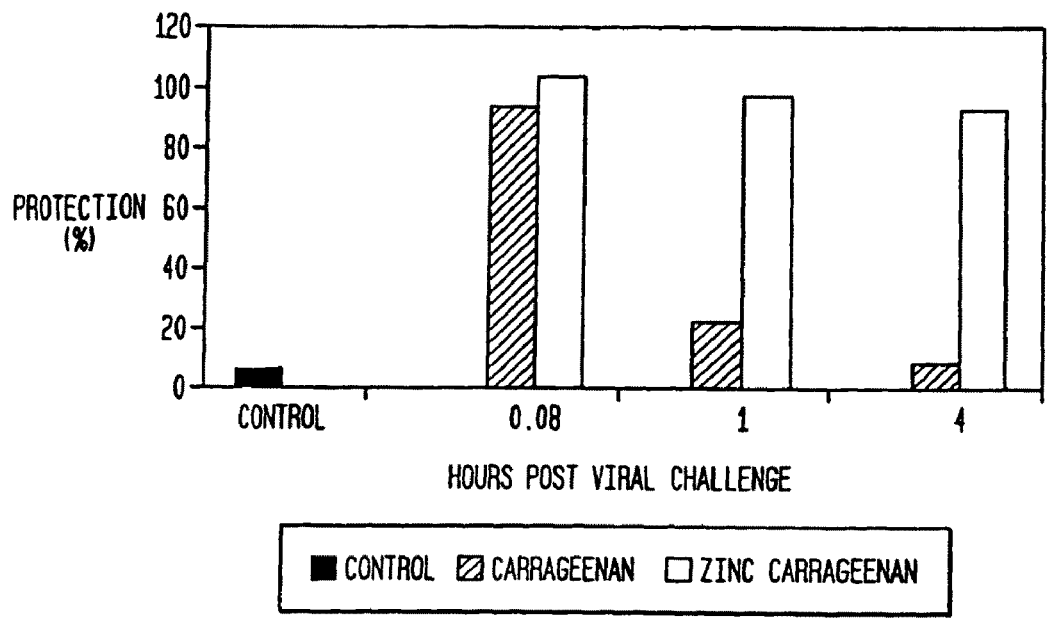
FIG. 9 is a graph showing protection against viral challenge by a composition containing the carrageenans of the present invention, and another composition of the present invention that contains zinc-carrageenan.

A microbicide that was able to be effective even if administered following exposure to a virus would extend product use to include women who were not able to use the product until after intercourse had already occurred e.g., women who fell victim to rape. Previously, researchers have been unable to identify a microbicide that might afford such protection. Zn-carrageenan is able to afford protection against HSV-2 infection in mice post-viral challenge. As the data below demonstrate, Zn-carrageenan is exceptional in that it demonstrated activity for up to 4 hours post-viral exposure (see FIG. 9). This finding is remarkable in light of Applicants' observations that K-II/λ carrageenan composition did not prevent infection post viral challenge unless administered immediately following HSV-2 challenge.

Example 17

Contraceptive Microbicide for Dual Protection

The K-II/λ carrageenan composition remains in the vagina for up to 24 hours, enabling a once-daily application for protection against HIV and its use as a vaginal delivery system for a contraceptive hormone. The feasibility of delivering various steroids vaginally has been thoroughly investigated with the recent development of contraceptive vaginal rings[43]. It has been shown that steroids applied directly to the vaginal mucosa are quickly absorbed, and only very small doses are needed to achieve the desired contraceptive effect[48-52]. In addition, vaginal delivery is usually accompanied by diminished undesirable side effects that are often associated with oral contraceptives.

The vaginal formulations of the present invention provide dual protection as a combination microbicide/contraceptive that have a further advantage of enhancing user motivation for compliance. The contraceptive hormone NES is a preferred contraceptive agent. This synthetic progestin has been shown to be an exceptionally potent molecule. Using classic bioassays of measuring the progestational potency, NES has proven to be 100 times more active than progesterone and only very small quantities of NES are required to suppress luteal activity. Additionally, extensive toxicology studies of NES have been conducted.

Example 18

Diffusion of NES from the K/λ Carrageenan Mixture

In order for the formulation containing the K-II/λ carrageenan composition and NES (hereinafter "CARRA/NES") to be an effective contraceptive, it is essential that NES be released from the carrageenan and absorbed through the vagina. We have carried out in vitro assays to determine if NES is released from CARRA/NES.

Figure 10:
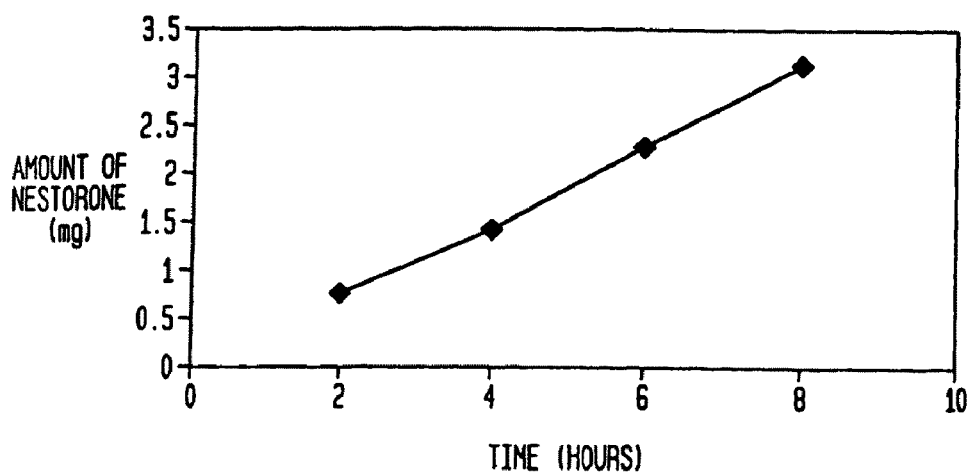
FIG. 10 is a graph of the amount of Nestorone released from a composition containing the carrageenans of the present invention.

We examined diffusion of NES through a dialysis membrane with a molecular weight cutoff of 1000. The molecular weight of NES is 370. NES diffused from the dialysis bag at a constant rate, as measured by HPLC. Results are illustrated in FIG. 10. These results demonstrate that NES is not bound to carrageenan. However, the rate of diffusion observed through the dialysis membrane cannot be related to the rate of diffusion that would be observed in the human vagina as the rate of diffusion was dependant on the surface area of the dialysis bag. Conditions in the vagina would be different.

We also conducted an experiment that involved centrifuging CARRA/NES through an Ultrafree-15 centrifugal filter and tube assembly at 2000 g for 99 minutes, to calculate percentage of NES released. The centrifuge filter is a device that fits into a centrifuge tube. The device has a flouted filter in the bottom that allows molecules with MW under 500 to pass through. Using this device, over 98% of the added NES was recovered in filtrate. This experiment confirms that NES is not bound to carrageenan.

Example 19

CARRA/NES (Release Rates)

CARRA/NES
Solutions of increasing concentrations of NES were formulated into the K-II/λ carrageenan composition to establish compatibility of the two compounds. A concentration of 500 μg/mL of NES in the K-II/λ carrageenan composition retained the rheological properties, as measured by pH, viscosity, homogeneity and ocular appearance, and exhibited retention of strength, as measured by the HSV-2/mouse assay. This concentration of NES is 40 times higher than the predicted concentration needed for a high-dose formulation of 100 pg/mL.

Diffusion of NES from CARRA/NES was investigated by two different methods, membrane dialysis and Ultrafree-15 centrifugation. In the membrane dialysis experiments, the membrane cutoff is 1,000, and diffusion of NES was measured by HPLC. Results indicate that NES is not bound to the negatively charged carrageenan and, although the rate of diffusion through a dialysis membrane is different than in vivo systemic absorption, diffusion occurs in a time dependent manner. In the Ultrafree-15 centrifugation experiments, a Millipore, Ultrafree-15 centrifugal filter and tube assembly was employed, which allows the passage of molecules of a MW<500 pass through; NES MW is 370. The use of this technique demonstrated that 98.6% of NES was recovered.

Example 20

Zn/Carrageenan/MIV-150

The combination of the most preferred carrageenans of the present invention along with zinc acetate as the water-soluble metal and MIV-150 as the NNRTI was compared with combinations of zinc/carrageenan (PC-707), MIV-150/carrageenan (PC-815), and carrageenan (Carraguard®). In particular, when animals were challenged with SHIV-RT 8 hours or 24 hours after the last dose of each of these gels, PC-707 and PC-815 separately blocked vaginal SHIV-RT infection at about the same level as Carraguard® (with a p value of greater than 0.05) at the same time at both time points PC-1005 blocked vaginal SHIV-RT infection better than these compounds (with a p value of less than 0.03). Thus, although PC-707 and PC-815 did block vaginal SHIV-RT infection to some extent for up to 24 hours, it was not predictable that the combination of zinc acetate, carrageenans and MIV-150 would totally block vaginal SHIV-RT infection for up to 24 hours.

The experimental procedures were carried out as follows:

A 700 mL glass mixing jar was charged with 1.5 grams of zinc acetate dihydrate, 15.0 grams of the carrageenans (in this case 95% lambda carrageenan and 5% kappa carrageenan), and 300.3 grams of sterile purified water. The contents were mixed with an overhead stirrer at 300 rpm for three hours at ambient temperature. Separately, a 250 ml Erlenmeyer flask was charged with 1.0 grams of methyl paraben and 150.9 grams of sterile purified water. The Erlenmeyer flask was heated to 60° C. with stirring to afford a clear solution, and the contents of the flask were immediately added to the zinc-carrageenan water mixture contained in the 700 ml mixing jar. The mixture was stirred for two hours at ambient temperature at which time 5 mL of an MIV-150/DMSO stock solution prepared by dissolving 18.5 mg of MIV-150 in 10 mL of dimethyl sulfoxide were added to the contents of the 700 mL mixing jar. This mixture was then stirred at 300 rpm for 35 minutes at ambient temperature, and 26 grams of sterile purified water was then added to the mixing jar and the contents were stirred for 30 minutes at ambient temperature.

Macaques were injected with Depo-Provera and three week later given 2 mL of the gel prepared as discussed above per day for two weeks prior to being challenged with 1,000 $TCID_{50}$ of SHIV-RT at the indicated times after the last gel was applied. The numbers of infected animals as set forth in Table 1 below reflect the number with typical viremia (SIV RNA copies in plasma).

TABLE 1

Repeated application of PC-1005 protects against vaginal SHIV-RT infection for up to 24 h

| Microbicide# | Challenge post last Gel Application | Number Infected/Total | Percent Infected | Significance^ (p value; MC vs test) | Significance^ (p value; Carr vs test) |
|---|---|---|---|---|---|
| MC | 4 h, 8 h, 24 h | 12/14 | 85.71% | | |
| PC-1005 | 4 h | 0/7 | 0% | <0.0003 | |
| Carraguard | 8 h | 5/7 | 71.43% | <0.6 | |
| PC-815 | 8 h | 2/7 | 28.57% | <0.02 | <0.3 |
| PC-707 | 8 h | 1/7 | 14.29% | <0.004 | <0.2 |
| PC-1005 | 8 h | 0/7 | 0% | <0.0003 | <0.03 |
| Carraguard | 24 h | 4/7 | 57.1% | <0.3 | |
| PC-815 | 24 h | 4/7 | 57.1% | <0.3 | |
| PC-707 | 24 h | 2/7 | 28.57% | <0.02 | <0.3 |
| PC-1005 | 24 h | 0/7 | 0% | <0.0003 | <0.03 |

MC = Methyl cellulose placebo; PC-707 = Carraguard + 0.3% zinc acetate; PC-815 = Carraguard + 50 μM MIV-150; PC-1005 = Carraguard + 0.3% zinc acetate + 50 μM MIV-150
^Calculated using Fisher's exact tests

REFERENCES

1. Butini, L. et al. Intercellular adhesion molecules (ICAM)-1, ICAM-2 and ICAM-3 function as counter receptors for lymphocyte function-associated molecule 1 in human immunodeficiency virus-mediated syncytia formation. *Eur J Immunol* 24, 2191-2195 (1994).
2. Food and Drug Administration. GRAS (Generally recognized as safe) food ingredients: Carrageenan. FDA Publications PB-221 206, (1972).
3. Benitz, K. F., Abraham, R., Golberg, L. & Coulston, F. Carrageenan: an ulcerogenic agent. *Toxicol. Appi. Pharmacol.* 22, 282 (1972).
4. Fox, M. R. S. & Jacobs, R. M. Metal Ions in Biological Systems., pp. 214-248 (Marcel Decker, Inc., 1986).
5. Luscombe, D. K. & Nicholls, P. J. Acute and subacute oral toxicity of AHR-2438B, a purified sodium lignosulphonate in rats. *Fd. Cosmet. Toxicol.* 11, 229-237 (1973).
6. Naess, B. The effect of microbial and animal proteinases on peptide- and protein lignosulphonic acid complexes in agar gel. Acta Vet. Scand. 12, 592-600. 1971. Ref Type: Abstract
7. Samman, S. & Roberts, D. C. K. The effect of zinc supplements on plasma zinc and copper levels and the reported symptoms in healthy volunteers. *Med. J. Australia* 146, 246-249 (1987).
8. U.S. EPA. Health Effects Assessment of for Zinc (and Compounds). EPA/540-1-96-048. 1984. Washington, D.C., US Environmental Protection Agency, Office of Research and Development. Ref Type: Data File
9. Walden, J. T. & Derreth, D. FDA New Release 72/55. *FDA Publications* 72/55, (1972).
10. Walker, A. P. et al. Test guidelines for the assessment of skin tolerance of potentially irritant cosmetic ingredients in man. *Fd. Chem. Toxic.* 35, 1099-1106 (1997).
11. Weiner, M. L. Intestinal transport of some macromolecules in food. *Fd. Chem. Toxic.* 26, 10, 867-880 (1988).
12. Food and Drug Administration. Study of mutagenic effects of calcium carrageenan (FDA No. 71-5). FDA Publications PB-221 820, (1972).
13. Elias, C. J. et al. Colposcopic Evaluation of a Vaginal Gel Formulation of iota-Carrageenan. *Contraception* 56, 387-389 (1997).
14. Lines, A. D. Value of the K+ Salt of Carrageenan as an Agar Substitute in Routine Bacteriological Media. *Applied and Environmental Microbiology* 34, 637-639 (1977).
15. Phillips, D. M. & Tan, X. Mechanism of trophoblast infection by HIV. *AIDS Res Hum Retroviruses* 9, 1697-1705 (1992).
16. Baba, M. et al. Pentosan polysulfate, a sulfated oligosaccharide, is a potent and selective anti-HIV agent in vitro. *Antiviral Res* 9, 335-343 (1988).
17. Baba, M. et al. Mechanism of inhibitory effect of dextran sulfate and heparin on replication of human immunodeficiency virus in vitro. *Proc Natl Acad Sci* 85, 6132-6126 (1988).
18. Pearce-Pratt, R. & Phillips, D. M. Studies of adhesion of lymphocytic cells: Implications for sexual transmission of human immunodeficiency virus. *Biol Reprod* 48, 431-445 (1993).

19. Pearce-Pratt, R. & Phillips, D. M. Sulfated polysaccharides inhibit lymphocyte-to-epithelial transmission of HIV-1. *Biol Reprod* 54, 173-182 (1996).
20. Maguire, R. A., Zacharopoulos, V. R. & Phillips, D. M. Carrageenan-N9 Spermicides for Preventing Pregnancy and Sexually Transmitted Infections. *Sex Transm Dis* 25, 494-500 (1998).
21. Phillips, D. M. Perspectives in Drug Discovery and Design. Fantini, J. & Sabatier, J. M. (eds.), pp. 213-223 (1996).
22. Zacharopoulos, V. R. & Phillips, D. M. Vaginal formulations of carrageenan protect mice from herpes simplex virus infection. *Clin. Diag. Lab. Immunol.* 4, 465-468 (1997).
23. Phillips, D. M. & Zacharopoulos, V. R. Nonoxynol-9 Enhances Rectal Infection by Herpes Simplex Virus in Mice. *Contraception* 57, 341-348 (1998).
24. Masuner, C. et al. Dendritic cells route Human Immunodeficiency Virus to lymph nodes after vaginal or intravenous administration to mice. *J Virol* 72, 7822-7829 (1998).
25. Masuner, C. et al. Dendritic Cells in Fundamental and Clinical Immunology. Ricciardi-Castagnoli (ed.), pp. 411-414 (Plenum Press, New York, 1997).
26. Anderson, D. J. Mechanisms of HIV-1 transmission via semen. *J. NIH Res.* 4, 104-111 (1992).
27. Levy, J. A. The transmission of AIDS: the case of the infected cell. *JAMA* 259, 3037-3038 (1988).
28. Zacharopoulos, V. R., Perotti, M. E. & Phillips, D. M. A role for cell migration in the sexual transmission of HIV? *Current Biol.* 7, 534-537 (1997).
29. Howett M. K., K. J. W. C. K. D. Human xenografts. A model system for human papillomavirus infection. *Intervir.* 31, 109-115 (1990).
30. Jerse, A. E. Experimental gonococcal genital tract infection and opacity protein expression in estradio-treat mice. *Infect Immun* 67, 5699-5708 (1999).
31. Kolopp, M. et al. Predictive value of an in vitro model for skin irritation (SkinEthic) applied to the testing of topical vehicles for SDZ ASM 981. Proc. Clin. Dermatol. 2000 Singapore 141. 1998. Ref Type: Abstract
32. Mitsuya, H. et al. Dextran sulfate suppression of viruses in the HIV family: inhibition of virion binding to CD4+ cells. *Science* 240, 646-649 (1988).
33. Suzuki H, T. T. I. K. Y. S. Y. N. T. S. Lignosulfonate, a water-solubilized lignin from the waste liquor of the pulping process, inhibits the infectivity and cytopathic effects of Human Immunodeficiency Virus in Vitro. *Agric Bid Chem* 53, 3369-3372 (1989).
34. Baba, M., Schols, D., Pauwels, R., Nakashima, H. & De Clercq, E. Sulfated polysaccharides as potent inhibitors of HIV-induced syncytium formation: a new strategy towards ADS chemotherapy. *JAIDS* 3, 493-499 (1990).
35. NRC (National Research Council). Recommended Dietary Allowances. (National Academy Press, Washington D.C., 1989).
36. Nicklin, S. & Miller, K. Effect of orally administered food-grade carrageenans on antibody-mediated and cell-mediated immunity in the inbred rat. *Fd. Chem. Toxic.* 22, 8, 615-621 (1984).
37. CEAMSA (Compania Espanola de Algas Marmnas, S. A. Technical Information 1999-2000. 1999. South America. Ref Type: Data File
38. ATSDR (Agency for Toxic Substances and Disease Registry). Toxological Profile for Zinc. *Agency for Toxic Substances and Disease Registry, U. S. Public Health Service, Atlanta, Ga.* 121 pp (2001).
39. Haraguchi, Y., Sakurai, H., Hussain, S., Anner, B. & Hoshino, H. Inhibition of HIV-1 Infection by Zinc Group Metal Compounds. *Antiviral Res* 43, 123-133 (1999).
40. Sergio, W. Zinc Salts that may be Effective Against the ADS Virus HIV. *Medical Hypotheses* 26, 253 (1988).
41. Arens, M. & Travis, S. Zinc Salts Inactivate Clinical Isolates of Herpes Simplex Virus In Vitro. *J Clin Microbiol* 38, 1758-1762 (2000).
42. Tennican, P., Carl, G., Frey, J., Thies, C. & Chvapil, M. Topical Zinc in the Treatment of Mice Infected Intravaginally with Herpes Genitalis Virus. *Proceedings of the Society for Experimental Biology and Medicine* 164, 593-597 (1980).
43. Alvarez-Sanchez, F., Brache, V., Jackanicz, T. & Faundes, A. Evaluation of four different contraceptive vaginal rings: steroid serum levels, luteal activity, bleeding control and lipid profiles. *Contraception* 46, 387-397 (1992).
44. Mishell, D. J., Lumkin, M. & Jackanicz, T. Initial clinical studies of intravaginal rings containing norethindrone and norgestrel. *Contraception* 12, 253 (1975).
45. Ballagh, S., Mishell, D., Jackanicz, T., Lacarra, M. & Eggena, P. Dose-finding study of a contraceptive ring releasing norethindrone acetate/ethinyl-estradiol. *Contraception* 50, 535-549 (1994).
46. Sivin, I., Mishell, D. J., Victor, A. & et al. A multicenter study of levonorgestrelestradiol contraceptive vaginal rings I—use of effectiveness. *Contraception* 24, 341-358 (1981).
47. Sivin, I., Mishell, D. J., Victor, A. & et al. A multicenter study of levonorgestrelestradiol contraceptive vaginal rings II—subjective and objective measures of effects. An international comparative trial. *Contraception* 24, 359-376 (2001).
48. Fanchin R et al. Transvaginal administration of progesterone: dose-response data support a first uterine pass effect. Obstet Gynecol 90, 396-40 1 (1997).
49. Cicinelli, E., Cignarelli, M., Sabatelli, S. & et al. Plasma concentrations of progesterone are higher in the uterine artery than in the radial artery after vaginal administration of hicronized progesterone in an oil-based solution to postmenopausal women. *Fertil Steril* 69, 471-473 (1998).
50. Rigg, L., Milanes, B., Villanueva & Yen, S. Efficacy of intravaginal and intranasal administration of micronized estradiol-17B. JCE&M 45, 1261-1264 (1977).
51. Martin, P. et al. Estradiol, estrone, and gonadotropin levels after use of vaginal estradiol. Obstet & Gyn 63, 441-444 (1984).
52. Schiff, I., Tulchinsky, D. & Yan, K. Vaginal absorption of esterone and 17B-estradiol. *Fertil Steril* 28, 1063-1066 (1977).
53. Kumar, N., Koide, S., Tsong Y & Sundaram, K. Nestorone: a progestin with a unique pharmacologic profile. *Steroid* 65, 629-636 (2000).
54. Odlind, V., Lithell, H., Selinus, I. & Vessby, B. Unaltered lipoprotein and carbohydrate metabolism during treatment with contraceptive subdermal implants containing 5T1435. *Contraception* 31, 130 (1985).
55. Robins, A. & Bardin, C. Nestorone Progestin—the ideal progestin for use in controlled release delivery systems. Ann N Y Acad Sci 828, 38-46 (1997).
56. Massai, R., Diaz 5, Jackanicz, T. & Croxatto R B. Vaginal rings for contraception in lactating women. *Steroid* 65, 703-707 (2000).
57. Lahteenmaki P L A, Daz 5, Miranda P & Croxatto K B. Milk and plasma concentrations of the progestin ST 1435 in women treated parenterally with ST 1435. *Contraception* 42, 555-562 (1990).

58. World Health Organization. Microdose intravaginal levonorgestrel contraception: a multicentered clinical trial I. *Contraception* 41, 105-124 (1990).
59. Yen, S. Reproductive Endocrinology. Yen S S C and Jaffe R B (ed.), pp. 200-236 (W.B. Saunders Co, Philadelphia, 1986).
60. Henzl, M. Reproductive Endocrinology. Yen S S C and Jaffe R B (ed.), pp. 243-682 (W.B. Saunders Co., Philadelphia, 1986).
61. Brache V. et al. Ovarian function during use of vaginal rings delivering three different doses of Nestorone. Contraception. 2001. Ref Type: In Press
62. Fraser I et al. Vaginal epithelial surface appearances in women using vaginal rings for contraception. *Contraception* 61, 13 1-138 (2000).
63. Couch, R. C. A 12-month systemic toxicity study of subdermal implant for 5T1435 in female cynomolous monkeys. New Mexico Regional Primate Research Laboratory, Mew Mexico State University Holloman AFB New Mexico. Population Council Files. 1992. Ref Type: Unpublished Work
64. Lahteenmaki, P., Weiner, E., Johansson, E. & Luukkainen, T. Contraception with subcutaneous capsules containing 5T1435. Pituitary and ovarian function and plasma levels of 5t1435. *Contraception* 23, 63-75 (1981).
65. Lahteenmaki P, Weiner E, Johansson E & Luukkainen T. Pituitary and ovarian function during contraception with one subcutaneous implant releasing a progestin, 5T1435. *Contraception* 25, 299-306 (1982).
66. Haukkamaa, M., Laurikka-Routti, M. & Heikinheimo, O. Transdermal absorption of the progestin 5T1435: Therapeutic serum steroid concentrations and high excretion of the steroid in saliva. Contraception 44, 269-276 (1991).
67. Laurikka-Routti, M., Haukkamaa, M. & Lahteenmaki, P. Suppression of ovarian function with the transdermally given synthetic progestin 5T1435. Fertil Steril 58, 680-684 (1992).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An aqueous antimicrobial composition comprising an effective amount of an antimicrobial agent comprising carrageenans which are lambda carrageenan in an amount of at least about 50% by dry weight of said carrageenans, the remainder of said carrageenans being at least one non-lambda carrageenan, and a physiologically acceptable water-soluble zinc salt, and the antiretroviral, non-nucleoside reverse transcriptase inhibitor, MIV-150.

2. The antimicrobial composition of claim 1 including a physiologically acceptable pH controlling agent.

3. The antimicrobial composition of claim 1 including a physiologically acceptable preservative.

4. The antimicrobial composition of claim 2 wherein said physiologically acceptable pH controlling agent is selected from the group consisting of acetate, citrate and lactate buffers.

5. The antimicrobial composition of claim 4 wherein said acetate buffer comprises a mixture of acetic acid and sodium acetate.

6. The antimicrobial composition of claim 4 wherein said citrate buffer comprises a mixture of citric acid and sodium citrate.

7. The antimicrobial composition of claim 4 wherein said lactate buffer comprises a mixture of lactic acid and sodium lactate.

8. The antimicrobial composition of claim 3 wherein said physiologically acceptable preservative comprises methyl paraben.

9. The antimicrobial composition of claim 1 wherein said MIV-150 is present in amounts of from about 5 µM to 5,000 µM.

10. The antimicrobial composition of claim 9 wherein said MIV-150 is present in amounts of from about 20 µM to 250 µM.

11. The antimicrobial composition of claim 1 wherein said effective amount of said antimicrobial agent is about 1% to about 5% by total weight of said composition.

12. The antimicrobial composition of claim 11 wherein said effective amount of said antimicrobial agent is about 3% by total weight of said composition.

13. The antimicrobial composition of claim 1 having a pH of about 3.5 to about 8.5.

14. The antimicrobial composition of claim 13 wherein the pH is about 6.8 to about 7.2.

15. The antimicrobial composition of claim 1 wherein said zinc salt is zinc acetate.

16. The antimicrobial composition of claim 1 wherein said zinc salt is zinc lactate.

17. The antimicrobial composition of claim 1 wherein said zinc salt is present in an amount of from about 0.03% to about 1.5% based on the total weight of said composition.

18. The antimicrobial composition of claim 17 wherein said zinc salt is present in an amount of from about 0.3% to about 1.0% based on the total weight of said composition.

* * * * *